United States Patent  (10) Patent No.: US 8,211,369 B2
Urlaub et al.  (45) Date of Patent: Jul. 3, 2012

(54) HIGH SURFACE AREA MATERIAL BLENDS FOR ODOR REDUCTION, ARTICLES UTILIZING SUCH BLENDS AND METHODS OF USING SAME

(75) Inventors: John Jerald Urlaub, Lake Stevens, WA (US); John Gavin MacDonald, Decatur, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 615 days.

(21) Appl. No.: 12/368,503

(22) Filed: Feb. 10, 2009

(65) Prior Publication Data

US 2009/0142224 A1  Jun. 4, 2009

Related U.S. Application Data

(62) Division of application No. 10/687,004, filed on Oct. 16, 2003, now Pat. No. 7,488,520.

(51) Int. Cl.
*A61L 9/18* (2006.01)

(52) U.S. Cl. ............................. 422/122; 422/5; 428/34.1

(58) Field of Classification Search .............. 422/5, 122; 428/34.1, 34.4, 34.5
See application file for complete search history.

(56) References Cited

U.S. PATENT DOCUMENTS

| | | | |
|---|---|---|---|
| 2,015,864 A | 10/1935 | Müller et al. |
| 2,593,146 A | 4/1952 | Howard |
| 3,266,973 A | 8/1966 | Crowley |
| 3,338,992 A | 8/1967 | Kinney |
| 3,341,394 A | 9/1967 | Kinney |
| 3,381,688 A | 5/1968 | Satas |
| 3,494,821 A | 2/1970 | Evans |
| 3,502,538 A | 3/1970 | Petersen |
| 3,502,763 A | 3/1970 | Hartmann |
| 3,507,269 A | 4/1970 | Berry |
| 3,542,615 A | 11/1970 | Dobo et al. |
| 3,615,478 A | 10/1971 | Hoshino et al. |
| 3,692,618 A | 9/1972 | Dorschner et al. |
| 3,794,497 A | 2/1974 | Pratt et al. |
| 3,802,817 A | 4/1974 | Matsuki et al. |
| 3,836,633 A | 9/1974 | Beschke |
| 3,849,241 A | 11/1974 | Butin et al. |
| 3,919,437 A | 11/1975 | Brown et al. |
| 3,933,666 A | 1/1976 | Yoneno et al. |
| 3,960,494 A | 6/1976 | Verma et al. |
| 3,971,665 A | 7/1976 | Suzuki et al. |
| 4,006,030 A | 2/1977 | Yoshida et al. |

(Continued)

FOREIGN PATENT DOCUMENTS

EP  0103214 A2  3/1984
(Continued)

OTHER PUBLICATIONS

Abstract of Japanese Patent No. JP63072337, Apr. 2, 1988.

(Continued)

*Primary Examiner* — Sean E Conley
(74) *Attorney, Agent, or Firm* — Dority & Manning, P.A.

(57) ABSTRACT

A method for neutralizing odor contained within the headspace of product packaging includes the steps of formulating a blend of either modified and unmodified high surface area materials, differently modified high surface area materials, different unmodified high surface area materials, or a combination thereof; applying the blend of high surface area materials to the inside of the product packaging.

22 Claims, 3 Drawing Sheets

U.S. PATENT DOCUMENTS

| | | |
|---|---|---|
| 4,041,203 A | 8/1977 | Brock et al. |
| 4,078,029 A | 3/1978 | Yoshida et al. |
| 4,089,646 A | 5/1978 | Habereder et al. |
| 4,100,324 A | 7/1978 | Anderson et al. |
| 4,101,638 A | 7/1978 | Inoue et al. |
| 4,144,370 A | 3/1979 | Boulton |
| 4,172,781 A | 10/1979 | Walk et al. |
| 4,297,233 A | 10/1981 | Gualandi |
| RE30,797 E | 11/1981 | Davis |
| RE30,803 E | 11/1981 | Davis |
| 4,313,820 A | 2/1982 | Farha, Jr. et al. |
| 4,340,563 A | 7/1982 | Appel et al. |
| 4,375,448 A | 3/1983 | Appel et al. |
| 4,407,960 A | 10/1983 | Tratnyek |
| 4,467,012 A | 8/1984 | Pedersen et al. |
| 4,469,746 A | 9/1984 | Weisman et al. |
| 4,488,969 A | 12/1984 | Hou |
| 4,494,278 A | 1/1985 | Kroyer et al. |
| 4,494,629 A | 1/1985 | Raeburn |
| 4,517,308 A | 5/1985 | Ehlenz et al. |
| 4,522,203 A | 6/1985 | Mays |
| 4,525,410 A | 6/1985 | Haqiwara et al. |
| 4,575,556 A | 3/1986 | Byrne et al. |
| 4,604,313 A | 8/1986 | McFarland et al. |
| 4,640,810 A | 2/1987 | Laursen et al. |
| 4,643,801 A | 2/1987 | Johnson |
| 4,655,757 A | 4/1987 | McFarland et al. |
| 4,701,218 A | 10/1987 | Barker et al. |
| 4,715,983 A | 12/1987 | Ota et al. |
| 4,725,415 A | 2/1988 | Kidd |
| 4,734,324 A | 3/1988 | Hill |
| RE32,649 E | 4/1988 | Brandt et al. |
| 4,775,585 A | 10/1988 | Hagiwara et al. |
| 4,780,448 A | 10/1988 | Broecker et al. |
| 4,781,858 A | 11/1988 | Mizukami et al. |
| 4,783,220 A | 11/1988 | Gamble et al. |
| 4,798,603 A | 1/1989 | Meyer et al. |
| 4,802,473 A | 2/1989 | Hubbard et al. |
| 4,818,464 A | 4/1989 | Lau |
| 4,823,404 A | 4/1989 | Morell et al. |
| 4,823,803 A | 4/1989 | Nakamura |
| RE32,957 E | 6/1989 | Elias |
| 4,904,304 A | 2/1990 | Watanabe et al. |
| 4,969,457 A | 11/1990 | Hubbard et al. |
| 4,978,615 A | 12/1990 | Aoyama et al. |
| 4,988,505 A | 1/1991 | Watanabe et al. |
| 5,000,746 A | 3/1991 | Meiss |
| 5,020,533 A | 6/1991 | Hubbard et al. |
| 5,057,302 A | 10/1991 | Johnson et al. |
| 5,064,473 A | 11/1991 | Kubo et al. |
| 5,100,581 A | 3/1992 | Watanabe et al. |
| 5,100,702 A | 3/1992 | Maeda et al. |
| 5,108,739 A | 4/1992 | Kurihara et al. |
| 5,122,418 A | 6/1992 | Nakane et al. |
| 5,133,803 A | 7/1992 | Moffatt |
| 5,145,518 A | 9/1992 | Winnik et al. |
| 5,145,727 A | 9/1992 | Potts et al. |
| 5,169,706 A | 12/1992 | Collier, IV et al. |
| 5,178,931 A | 1/1993 | Perkins et al. |
| 5,183,656 A | 2/1993 | Uesaka et al. |
| 5,188,885 A | 2/1993 | Timmons et al. |
| 5,196,177 A | 3/1993 | Watanabe et al. |
| 5,204,111 A | 4/1993 | Handjani et al. |
| 5,204,429 A | 4/1993 | Kaminsky et al. |
| 5,209,998 A | 5/1993 | Kavassalis et al. |
| 5,220,000 A | 6/1993 | Theodoropulos |
| 5,221,497 A | 6/1993 | Watanabe et al. |
| 5,225,374 A | 7/1993 | Fare et al. |
| 5,230,953 A | 7/1993 | Tsugeno et al. |
| 5,238,518 A | 8/1993 | Okubi et al. |
| 5,245,117 A | 9/1993 | Withers et al. |
| 5,266,289 A | 11/1993 | Tsugeno et al. |
| 5,284,703 A | 2/1994 | Everhart et al. |
| 5,292,868 A | 3/1994 | Subramanian |
| 5,294,717 A | 3/1994 | Theodoropulos |
| 5,300,365 A | 4/1994 | Ogale |
| 5,322,061 A | 6/1994 | Brunson |
| 5,332,432 A | 7/1994 | Okubi et al. |
| 5,338,713 A | 8/1994 | Takagi et al. |
| 5,342,876 A | 8/1994 | Abe et al. |
| 5,350,624 A | 9/1994 | Georger et al. |
| 5,366,947 A | 11/1994 | Müller et al. |
| 5,382,400 A | 1/1995 | Pike et al. |
| 5,383,450 A | 1/1995 | Hubbard et al. |
| 5,397,667 A | 3/1995 | Law et al. |
| 5,407,442 A | 4/1995 | Karapasha |
| 5,407,600 A | 4/1995 | Ando et al. |
| 5,420,090 A | 5/1995 | Spencer et al. |
| 5,427,844 A | 6/1995 | Murai et al. |
| 5,429,628 A | 7/1995 | Trinh et al. |
| 5,451,450 A | 9/1995 | Erderly et al. |
| 5,458,864 A | 10/1995 | Tsuegeno et al. |
| 5,472,775 A | 12/1995 | Obijeski et al. |
| 5,480,636 A | 1/1996 | Maruo et al. |
| 5,486,356 A | 1/1996 | Yim |
| 5,487,938 A | 1/1996 | Spencer et al. |
| 5,488,126 A | 1/1996 | Subramanian et al. |
| 5,527,171 A | 6/1996 | Soerensen |
| 5,538,548 A | 7/1996 | Yamazaki |
| 5,539,124 A | 7/1996 | Etherton et al. |
| 5,540,916 A | 7/1996 | Parks |
| 5,547,607 A | 8/1996 | Ando et al. |
| 5,553,608 A | 9/1996 | Reese et al. |
| 5,554,775 A | 9/1996 | Krishnamurti et al. |
| 5,580,655 A | 12/1996 | El-Shall et al. |
| 5,583,219 A | 12/1996 | Subramanian et al. |
| 5,591,797 A | 1/1997 | Barthel et al. |
| 5,597,512 A | 1/1997 | Watanabe et al. |
| 5,661,198 A | 8/1997 | Inatani et al. |
| 5,663,224 A | 9/1997 | Emmons et al. |
| 5,679,138 A | 10/1997 | Bishop et al. |
| 5,679,724 A | 10/1997 | Sacripante et al. |
| 5,695,868 A | 12/1997 | McCormack |
| 5,733,272 A | 3/1998 | Brunner et al. |
| 5,747,003 A | 5/1998 | Mohnot et al. |
| 5,773,227 A | 6/1998 | Kuhn et al. |
| 5,795,985 A | 8/1998 | Hüsler et al. |
| 5,813,398 A | 9/1998 | Baird et al. |
| 5,817,300 A | 10/1998 | Cook et al. |
| 5,837,352 A | 11/1998 | English et al. |
| 5,843,509 A | 12/1998 | Calvo Salve et al. |
| 5,855,788 A | 1/1999 | Everhart et al. |
| 5,861,144 A | 1/1999 | Peterson et al. |
| 5,871,872 A | 2/1999 | Matijevic et al. |
| 5,874,067 A | 2/1999 | Lucas et al. |
| 5,880,176 A | 3/1999 | Kamoto et al. |
| 5,880,309 A | 3/1999 | Suzuki et al. |
| 5,882,638 A | 3/1999 | Dodd et al. |
| 5,885,599 A | 3/1999 | Peterson et al. |
| 5,897,541 A | 4/1999 | Uitenbroek et al. |
| 5,902,226 A | 5/1999 | Tasaki et al. |
| 5,905,101 A | 5/1999 | Fujiki et al. |
| 5,916,596 A | 6/1999 | Desai et al. |
| 5,948,398 A | 9/1999 | Hanamoto et al. |
| 5,948,483 A | 9/1999 | Kim et al. |
| 5,962,566 A | 10/1999 | Grandfils et al. |
| 5,964,926 A | 10/1999 | Cohen |
| 5,972,389 A | 10/1999 | Shell et al. |
| 5,985,229 A | 11/1999 | Yamada et al. |
| 5,989,510 A | 11/1999 | Abe et al. |
| 5,989,515 A | 11/1999 | Watanabe et al. |
| 6,004,625 A | 12/1999 | Ohshima |
| 6,007,592 A | 12/1999 | Kasai et al. |
| 6,024,786 A | 2/2000 | Gore |
| 6,045,900 A | 4/2000 | Haffner et al. |
| 6,047,413 A | 4/2000 | Welchel et al. |
| 6,060,410 A | 5/2000 | Gillberg-LaForce et al. |
| 6,073,771 A | 6/2000 | Pressley et al. |
| 6,075,179 A | 6/2000 | McCormack et al. |
| 6,096,299 A | 8/2000 | Guarracino et al. |
| 6,111,163 A | 8/2000 | McCormack et al. |
| 6,172,173 B1 | 1/2001 | Spencer et al. |
| 6,177,608 B1 | 1/2001 | Weinstrauch |
| 6,190,814 B1 | 2/2001 | Law et al. |
| 6,193,844 B1 | 2/2001 | McLaughlin et al. |
| 6,225,524 B1 | 5/2001 | Guarracino et al. |
| 6,238,767 B1 | 5/2001 | McCormack et al. |

| | | |
|---|---|---|
| 6,254,894 B1 | 7/2001 | Denkewicz, Jr. et al. |
| 6,264,615 B1 | 7/2001 | Diamond et al. |
| 6,277,346 B1 | 8/2001 | Murasawa et al. |
| 6,277,772 B1 | 8/2001 | Gancet et al. |
| 6,291,535 B1 | 9/2001 | Watanabe et al. |
| 6,294,222 B1 | 9/2001 | Cohen et al. |
| 6,299,867 B1 | 10/2001 | Aoyagi et al. |
| 6,309,736 B1 | 10/2001 | McCormack et al. |
| 6,315,864 B2 | 11/2001 | Anderson et al. |
| 6,334,988 B1 | 1/2002 | Gallis et al. |
| 6,344,218 B1 | 2/2002 | Dodd et al. |
| 6,344,272 B1 | 2/2002 | Oldenburg et al. |
| 6,358,537 B1 | 3/2002 | Hoshino et al. |
| 6,358,909 B1 | 3/2002 | Ochomogo et al. |
| 6,369,290 B1 | 4/2002 | Glaug et al. |
| 6,376,741 B1 | 4/2002 | Guarracino et al. |
| 6,387,495 B1 | 5/2002 | Reeves et al. |
| 6,398,827 B1 | 6/2002 | Ota et al. |
| 6,410,765 B1 | 6/2002 | Wellinghoff et al. |
| 6,425,530 B1 | 7/2002 | Coakley |
| 6,427,693 B1 | 8/2002 | Blackstock et al. |
| 6,428,814 B1 | 8/2002 | Bosch et al. |
| 6,433,243 B1 | 8/2002 | Woltman et al. |
| 6,440,187 B1 | 8/2002 | Kasai et al. |
| 6,460,989 B1 | 10/2002 | Yano et al. |
| 6,461,735 B1 | 10/2002 | Furuya et al. |
| 6,467,897 B1 | 10/2002 | Wu et al. |
| 6,468,500 B1 | 10/2002 | Sakaguchi et al. |
| 6,475,601 B1 | 11/2002 | Sakaki et al. |
| 6,479,150 B1 | 11/2002 | Liu et al. |
| 6,491,790 B1 | 12/2002 | Proverb et al. |
| 6,498,000 B2 | 12/2002 | Murasawa et al. |
| 6,517,199 B1 | 2/2003 | Tomioka et al. |
| 6,531,704 B2 | 3/2003 | Yadav et al. |
| 6,536,890 B1 | 3/2003 | Kato et al. |
| 6,548,264 B1 * | 4/2003 | Tan et al. ............... 435/7.21 |
| 6,551,457 B2 | 4/2003 | Westman et al. |
| 6,562,441 B1 | 5/2003 | Maeda et al. |
| 6,575,383 B2 | 6/2003 | Dobler et al. |
| 6,578,521 B2 | 6/2003 | Raymond et al. |
| 6,589,562 B1 | 7/2003 | Shefer et al. |
| 6,607,711 B2 | 8/2003 | Pedersen |
| 6,623,848 B2 | 9/2003 | Brehm et al. |
| 6,638,918 B2 | 10/2003 | Davison et al. |
| 6,639,004 B2 | 10/2003 | Falat et al. |
| 6,645,569 B2 | 11/2003 | Cramer et al. |
| 6,693,071 B2 | 2/2004 | Ghosh et al. |
| 6,740,406 B2 | 5/2004 | Hu et al. |
| 7,141,518 B2 | 11/2006 | MacDonald et al. |
| 7,413,550 B2 | 8/2008 | MacDonald et al. |
| 7,438,875 B2 | 10/2008 | Do et al. |
| 2001/0000889 A1 | 5/2001 | Yadav et al. |
| 2001/0023338 A1 | 9/2001 | Guarracino et al. |
| 2001/0031248 A1 | 10/2001 | Hall-Puzio et al. |
| 2001/0056246 A1 | 12/2001 | Rodriguez-Fernandez |
| 2001/0056270 A1 * | 12/2001 | Mizutani et al. ......... 604/385.02 |
| 2002/0005145 A1 | 1/2002 | Sherman |
| 2002/0066542 A1 | 6/2002 | Jakob et al. |
| 2002/0091071 A1 | 7/2002 | Fischer et al. |
| 2002/0106466 A1 | 8/2002 | Hausmann et al. |
| 2002/0110686 A1 | 8/2002 | Dugan |
| 2002/0128336 A1 | 9/2002 | Kolb et al. |
| 2002/0142937 A1 | 10/2002 | Carter et al. |
| 2002/0149656 A1 | 10/2002 | Nohr et al. |
| 2002/0150678 A1 | 10/2002 | Cramer et al. |
| 2002/0176982 A1 | 11/2002 | Rohrbaugh et al. |
| 2002/0177621 A1 | 11/2002 | Hanada |
| 2002/0182102 A1 | 12/2002 | Fontenot et al. |
| 2003/0013369 A1 | 1/2003 | Soane et al. |
| 2003/0021983 A1 | 1/2003 | Nohr et al. |
| 2003/0050211 A1 | 3/2003 | Hage et al. |
| 2003/0056648 A1 | 3/2003 | Fornai et al. |
| 2003/0070782 A1 | 4/2003 | Proverb et al. |
| 2003/0082237 A1 | 5/2003 | Cha et al. |
| 2003/0100842 A1 | 5/2003 | Rosenberg et al. |
| 2003/0147956 A1 | 8/2003 | Shefer et al. |
| 2003/0147966 A1 | 8/2003 | Franzen et al. |
| 2003/0181540 A1 | 9/2003 | Quellet et al. |
| 2003/0203009 A1 | 10/2003 | MacDonald |
| 2003/0235605 A1 | 12/2003 | Lelah et al. |
| 2004/0033269 A1 | 2/2004 | Hei et al. |
| 2004/0034157 A1 | 2/2004 | Ghosh et al. |
| 2004/0043688 A1 | 3/2004 | Soerens et al. |
| 2004/0120904 A1 | 6/2004 | Lye et al. |
| 2004/0120921 A1 | 6/2004 | Quincy, III et al. |
| 2004/0122387 A1 | 6/2004 | Long et al. |
| 2004/0175556 A1 | 9/2004 | Clark et al. |
| 2005/0084412 A1 | 4/2005 | MacDonald et al. |
| 2005/0084464 A1 | 4/2005 | McGrath et al. |
| 2005/0084474 A1 | 4/2005 | Wu et al. |
| 2005/0084977 A1 | 4/2005 | Boga et al. |
| 2005/0112085 A1 | 5/2005 | MacDonald et al. |
| 2005/0113771 A1 | 5/2005 | MacDonald et al. |
| 2005/0131363 A1 | 6/2005 | MacDonald et al. |

FOREIGN PATENT DOCUMENTS

| | | |
|---|---|---|
| EP | 0103214 A3 | 3/1984 |
| EP | 0232141 A1 | 8/1987 |
| EP | 0251783 A2 | 1/1988 |
| EP | 0251783 A3 | 1/1988 |
| EP | 0282287 A2 | 9/1988 |
| EP | 0282287 A3 | 9/1988 |
| EP | 0339461 A1 | 11/1989 |
| EP | 0348978 A2 | 1/1990 |
| EP | 0376448 A1 | 7/1990 |
| EP | 0389015 A2 | 9/1990 |
| EP | 0389015 A3 | 9/1990 |
| EP | 0389023 A2 | 9/1990 |
| EP | 0389023 A3 | 9/1990 |
| EP | 0483500 A1 | 5/1992 |
| EP | 0510619 A1 | 10/1992 |
| EP | 0749295 A1 | 12/1996 |
| EP | 0972563 A1 | 1/2000 |
| EP | 1034800 A1 | 9/2000 |
| EP | 1053788 A1 | 11/2000 |
| EP | 1157672 A1 | 11/2001 |
| EP | 1162172 A1 | 12/2001 |
| EP | 1188854 A1 | 3/2002 |
| EP | 1214878 A1 | 6/2002 |
| EP | 1216675 A1 | 6/2002 |
| EP | 1298071 A1 | 4/2003 |
| EP | 1315526 B1 | 6/2003 |
| JP | 62149322 | 7/1987 |
| JP | 3221142 | 9/1991 |
| WO | 8902698 A1 | 4/1989 |
| WO | 9111977 A1 | 8/1991 |
| WO | 9112029 A1 | 8/1991 |
| WO | 9112030 A1 | 8/1991 |
| WO | 9619346 A2 | 6/1996 |
| WO | 9619346 A3 | 6/1996 |
| WO | 9725076 A1 | 7/1997 |
| WO | 9820915 A1 | 5/1998 |
| WO | 9826808 A2 | 6/1998 |
| WO | 9826808 A3 | 6/1998 |
| WO | 9947252 A2 | 9/1999 |
| WO | 9947252 A3 | 9/1999 |
| WO | 0003797 A1 | 1/2000 |
| WO | 0013764 A1 | 3/2000 |
| WO | 0029036 A2 | 5/2000 |
| WO | 0029036 A3 | 5/2000 |
| WO | 0059555 A1 | 10/2000 |
| WO | 0076558 A1 | 12/2000 |
| WO | 0106054 A1 | 1/2001 |
| WO | 0226272 A1 | 4/2002 |
| WO | 0249559 A2 | 6/2002 |
| WO | 0249559 A3 | 6/2002 |
| WO | 02055115 A1 | 7/2002 |
| WO | 02062881 A2 | 8/2002 |
| WO | 02062881 A3 | 8/2002 |
| WO | 02064877 A2 | 8/2002 |
| WO | 02064877 A3 | 8/2002 |
| WO | 02083297 A1 | 10/2002 |
| WO | 02084017 A1 | 10/2002 |
| WO | 02094329 A1 | 11/2002 |
| WO | 02095112 A1 | 11/2002 |
| WO | 03000979 A2 | 1/2003 |
| WO | 03000979 A3 | 1/2003 |
| WO | 03025067 A1 | 3/2003 |

| WO | 03032959 A1 | 4/2003 |
| WO | 03088931 A2 | 10/2003 |
| WO | 03088931 A3 | 10/2003 |
| WO | 03092885 A1 | 11/2003 |
| WO | 04000986 A1 | 12/2003 |

OTHER PUBLICATIONS

Abstract of Japanese Patent No. JP1262868, Oct. 19, 1989.
Abstract of Japanese Patent No. JP2157039, Jun. 15, 1990.
Abstract of Japanese Patent No. JP3195562, Aug. 27, 1991.
Abstract of Japanese Patent No. JP4255767, Sep. 10, 1992.
Abstract of Japanese Patent No. JP4335141, Nov. 24, 1992.
Abstract of Japanese Patent No. JP5098185, Apr. 20, 1993.
Abstract of Japanese Patent No. JP5106199, Apr. 27, 1993.
Abstract of Japanese Patent No. JP5261246, Oct. 12, 1993.
Abstract of Japanese Patent No. JP6285140, Oct. 11, 1994.
Abstract of Japanese Patent No. JP7256025, Oct. 9, 1995.
Abstract of Japanese Patent No. JP8152409, Jun. 11, 1996.
Abstract of Japanese Patent No. JP9143872, Jun. 3, 1997.
Abstract of SU834073, May 30, 1981.
Abstract of Article—*Non-hydrothermal synthesis of copper-, zinc- and copper-zinc hydrosilicates*, Vurieva, T.M. et al., Materials Research Innovations, vol. 5, No. 1, Jun. 2001, 2 pages.
Article—*Adsorption of Dyes on Nanosize Modified Silica Particles*, Guangwei Wu, Athanasia Koliadima, Yie-Shein Her, and Egon Matijevic, Journal of Colloid and Interface Sciences, vol. 195, 1997, pp. 222-228.
Article—*Adsorption of Gases in Multimolecular Layers*, Stephen Brunauer, P. H. Emmett, and Edward Teller, American Chemical Society, vol. 60, Jan.-Jun. 1938, pp. 309-319.
Article—*Adsorption of Proteins and Antibiotics on Porous Alumina Membranes*, Yi Hua Ma, Aseem Bansal, and William M. Clark, Fundamentals of Adsorption, vol. 80, 1992, pp. 389-396.
Article—*Ammonia vapour in the mouth as a diagnostic marker for Helicobacter pylori infection: preliminary "proof of principle" pharmacological investigations*, C. D. R. Dunn, M. Black, D. C. Cowell, C. Penault, N. M. Ratcliffe, R. Spence, and C. Teare, British Journal of Biomedical Science, vol. 58, 2001, pp. 66-76.
Article—*Applicability of a SPME Method for the Rapid Determination of VOCs*, Béné, A. et al., Chimia, 56, No. 6, 2002, ISSN 0009-4293, pp. 289-291.
Article—*Characterisation of Novel Modified Active Carbons and Marine Algal Biomass for the Selective Adsorption of Lead*, Malik, D.J. et al., Water Research, 36, 2002, pp. 1527-1538.
Article—*Development of novel dye-doped silica nanoparticles for biomarker application*, Santra, S. et al., Journal of Biomedical Optics, vol. 6, No. 2, Apr. 2001, pp. 160-166.
Article—*Fe-MCM-41 for Selective Epoxidation of Styrene with Hydrogen Peroxide*, Zhang, Q. et al., The Chemical Society of Japan, Chemistry Letters 2001, pp. 946-947.
Article—*From Cyclodextrin Assemblies to Porous Materials by Silica Templating*, Polarz, S. et al., Angew. Chem. Int. Ed., vol. 40, No. 23, 2001, pp. 4417-4421.
Article—*Grafting of Poly(ethylenimine) onto Mesylated Cellulose Acetate, Poly(methyl methacrylate) and Poly(vinyl chloride)*, Biermann, C. J. et al., Carbohydrate Polymers, vol. 12, 1990, pp. 323-327.
Article—*Immobilization of $(n-Bu_4N)_4W_{10}O_{32}$ on Mesoporous MCM-41 and Amorphous Silicas for Photocatalytic Oxidation of Cycloalkanes with Molecular Oxygen*, Maldotti, A. et al., Journal of Catalysis, vol. 209, 2002, pp. 210-216.
Article—*Immunization of mice with peptomers covalently couopled to aluminum oxide nanoparticles*, Andreas Frey, Nicholas Mantis, Pamela A. Kozlowski, Alison J. Quayle, Adriana Bajardi, Juana J. Perdomo, Frank A. Robey, and Marian R. Neutra, Vaccine, vol. 17, 1999, pp. 3007-3019.
Article—*Mesoporous Sieves with Unified Hybrid Inorganic/Organic Frameworks*, Melde, B.J. et al., Chem. Mater., vol. 11, No. 11, 1999, pp. 3302-3308.
Article—*Nanoparticles based on polyelectrolyte complexes: effect of structure and net charge on the sorption capacity for solved organic molecules*, Buchhammer, M. et al., Colloid Polym. Sci., vol. 278, 2000, pp. 841-847.
Article—*Purification and Characterization of Urease from Helicobacter pylori*, Bruce E. Dunn, Gail P. Campbell, Guillermo I. Perez-Perez, and Martin J. Blaser, The Journal of Biological Chemistry, vol. 265, No. 16, Jun. 5, 1990, pp. 9464-1990.
Article—*Saponins and Sapogenins. VIII. Surface Films of Echinocystic Acid and Derivatives*, Noller, C.R., The Journal of the American Chemical Society, vol. 60, 1938, 3 pages.
Article—*Significance of Ammonia in the Genesis of Gastric Epithelial Lesions Induced by Helicobacter pylori: An in vitro Study with Different Bacterial Strains and Urea Concentrations*, P. Sommi, V. Ricci, R. Fiocca, M. Romano, K.J. Ivey, E. Cova, E. Solcia, and U. Ventura, Digestion, vol. 57, 1996, pp. 299-304.
Article—*Significance of ammonia produced by Helicobacter pylori*, Shigeji Ito, Yoshihiro Kohli, Takuji Kato, Yoshimichi Abe, and Takashi Ueda, European Journal of Gastroenterology & Hepatology, vol. 6, No. 2, 1994, pp. 167-174.
Article—*Silanol Groups, Siloxane Bridges, and Physically Adsorbed Water*, Bergna, H.E., Editor, The Colloid Chemistry of Silica, American Chemical Society 200th National Meeting, Aug. 26-31, 1990, pp. 22-23 and pp. 52-59.
Article—*Spectrophotometric Assay of Thiols*, Peter C. Jocelyn, Methods in Enzymology, vol. 142, 1987, pp. 44-67.
Article—*Structure and properties of silica nanoclusters at high temperatures*, Schweigert, I.V. et al., The American Physical Society, Physical Review B, vol. 65, No. 235410, pp. 1-9.
Article—*Study of the urea thermal decomposition (pyrolsis) reaction and importance to cyanuric acid production*, Schaber, P.M. et al., American Laboratory, Aug. 1999, pp. 13-21.
Article—*Synthesis of porous Silica with help from cyclodextrin aggregates*, Antonietti, M., Max-Planck-Institut für Kolloid-und, Germany, 1 page.
Article—*Uniform Deposition of Ultrathin Polymer Films on the Surfaces of $Al_2O_3$ Nanoparticles by a Plasma Treatment*, Shi, D. et al., University of Cincinnati and University of Michigan, Jun. 2000, pp. 1-15.
Article—*Validation of $^{13}C$-Urea Breath Test for the Diagnosis of Helicobacter Pylori Infection in the Singapore Population*, T. S. Chua, K. M. Fock, E. K. Teo, T. M. Ng, Singapore Medical Journal, vol. 43, No. 8, 2002, pp. 408-411.
Pocket Guide to Digital Printing, Cost, F., Delmar Publishers, Albany, NY, ISBN 0-8273-7592-1, pp. 144-145.
Product Information Sheet for Snowtex®, 6 pages.
PCT Search Report for PCT/US03/32846, Jun. 7, 2004.
PCT Search Report for PCT/US03/39737, Jun. 18, 2004.
PCT Search Report and Written Opinion for PCT/US2004/011596, Aug. 30, 2004.
PCT Search Report and Written Opinion for PCT/US2004/016933, Nov. 2, 2004.
Related U.S. Patent Application.

* cited by examiner

HIGH SURFACE AREA MATERIAL BLENDS FOR ODOR REDUCTION, ARTICLES UTILIZING SUCH BLENDS AND METHODS OF USING SAME

RELATED APPLICATIONS

The present application is a divisional of U.S. application Ser. No. 10/687,004, filed on Oct. 16, 2003, which is incorporated herein in its entirety by reference thereto.

FIELD OF THE INVENTION

This invention relates to high surface area materials useful in neutralizing (i.e reducing or removing) gases and/or odorous compounds. The high surface area materials, such as nanoparticles, may be utilized in their unmodified state or modified by being associated with metal components, which high surface area materials can bind with gas molecules and/or odorous compounds by adsorption onto their surfaces.

BACKGROUND OF THE INVENTION

Many attempts have been made to formulate effective odor removal systems and various consumer products are now available for combating odorous compounds. Some products are designed to cover up odors by emitting stronger, more dominant odors. Examples of such consumer products include scented air freshener sprays and candles.

Another means for combating malodorous compounds, including ammonia, methyl mercaptan, trimethylamine, and other various sulfides and amines, is to remove these compounds from a medium by deodorizing agents that will absorb these compounds. In this regard consumer products may also include activated charcoal and sodium bicarbonate, two compounds commonly used to absorb odors. However, activated charcoal typically has a low deodorizing ability, especially for ammonia odors and when in the presence of moisture. Furthermore, the black color of charcoal lacks aesthetically pleasing characteristics and often is prohibitive for its usage in visually exposed product applications.

Sodium bicarbonate, and other white odor absorbents such as silica gel and zeolites, generally have a lower absorbency than activated charcoal and are therefore less effective. Titanium oxide particles are also useful in removing a few odors such as ammonia. It has been recognized that adding zinc oxy or silicon oxy compounds to the titanium oxide broadens the titanium oxide deodorizing capabilities. However, this approach is still limited by the photocatalytic nature of the titanium dioxide, which requires light in order to convert odorous compounds into non-odorous compounds.

In addition to the need to remove foul smelling compounds, there is also a need for products capable of removing gases that, while not necessarily malodorous, still might cause a negative effect. There is a further need for a gas and/or odor removal/neutralizing compound that is effective both dry and in solution. There is still a further need for an effective odor removal/neutralizing compound that can be used in various industrial and consumer products and that can be easily applied to various surfaces and materials.

In this regard, it has been determined that malodors may often be caused by numerous chemistries from a product manufacturing environment, and that methods that are somewhat effective for removing or reducing certain odors, are incapable or not well suited for the removal of others. There is therefore a need for targeted compositions for removing multiple odors.

Finally, with the addition of certain chemistries in the manufacturing processes of packaged products, such as packaged tissue or paper products, it is not uncommon for consumers to detect chemical odors upon the opening of such products prior to use of the product. Odors may accumulate in the headspace of such product packaging prior to use. For the purposes of this application, the term "headspace" shall refer to the empty space within a product packaging that does not contain the product itself, such as that empty space which lies between the product itself and the packaging, or that empty space between multiple products in a package. For example, for bathroom tissue and towel products, the headspace will include the space inside the hollow tissue or towel core rolls. There is therefore a need for a composition and method for removing such odors from product packaging, and in particular product packaging headspace, so as to provide consumers with a more satisfying experience in using such products. It is to such needs that the current invention is directed.

SUMMARY OF THE INVENTION

A method for neutralizing odor contained within the headspace of a product packaging includes the steps of formulating a blend of differently modified high surface area materials; and applying the blend of differently modified high surface area materials to the inside of a product packaging. For the purposes of this application, the phrase "inside of a product packaging" shall mean anywhere inside a package, such as for example, along the inside surface of a package, on a separate insert within the package, or alternatively, on a portion of a product contained within the package.

In an alternative embodiment, the method includes the step of sealing the product packaging so as to maintain the environment inside the product packaging.

In a further alternative embodiment, the method step of applying the blend is conducted by applying the blend to an insert which is then placed within the product packaging.

In still a further alternative embodiment, the method step of applying the blend is conducted by applying the blend to an inside surface of the product packaging.

In still a further alternative embodiment, the method step of applying the blend is conducted by applying the blend to a portion of the product contained in the product packaging.

In still a further alternative embodiment, a method for neutralizing odor contained within the headspace of a product packaging includes the steps of formulating a blend of modified and unmodified high surface area materials; and applying the blend of modified and unmodified high surface area materials to the inside of a product packaging.

In still a further alternative embodiment, a method for neutralizing odor contained within the headspace of a product packaging includes the steps of formulating a blend of unmodified and at least two differently modified high surface area materials; and applying the blend of modified and unmodified high surface area materials to the inside of a product packaging.

In still a further alternative embodiment an insert for inclusion within product packaging includes a coating of a blend of differently modified high surface area materials.

In still a further alternative embodiment an insert for inclusion within product packaging includes a coating of a blend of modified and unmodified high surface area materials.

In still a further alternative embodiment, a method for producing a packaged product which neutralizes head space odors contained between the product and the product packaging includes the steps of providing a product to be packaged; packaging said product within a packaging material along with a blend of either modified and unmodified high surface area materials or a blend of differently modified high surface area materials; and enclosing said product within the packaging material.

In still another alternative embodiment, a method for neutralizing odor contained within the headspace of a tissue/towel/or other rolled paper product packaging enclosing at least one tissue/towel or other rolled paper product having a core, includes the steps of formulating a blend of either modified and unmodified high surface area materials or differently modified high surface area materials; providing a core containing roll paper product; applying the blend of high surface area materials to the inside surface of the core containing rolled paper product; enclosing the core containing rolled paper product within a product packaging.

In still a further alternative embodiment, a package containing a product includes a product; packaging material which encloses the product within an enclosure formed by the packaging material; and a blend of differently modified nanoparticles contained within the packaging material enclosure, whereby as odor or gas is generated within the enclosure, it is adsorbed onto the surfaces of the nanoparticle blend.

In still a further alternative embodiment, a package containing a product includes a product, packaging material which encloses the product within an enclosure formed by the packaging material; and a blend of modified and unmodified nanoparticles contained within the packaging material enclosure; whereby, as odor or gas is generated within the enclosure, it is adsorbed onto the surfaces of the nanoparticle blend.

In still a further alternative embodiment a method for neutralizing odor contained within the headspace of a product packaging includes the steps of formulating a blend of differently modified high surface area materials, modified and unmodified high surface area materials, different unmodified high surface area materials or a combination thereof; applying the blend of high surface area materials to the inside of a product packaging.

In still a further alternative embodiment a package containing a product includes a product; packaging material which encloses the product within an enclosure formed by the packaging material; and a blend of either modified and unmodified nanoparticles, differently modified nanoparticles, different unmodified nanoparticles or a combination thereof with blend contained within the packaging material enclosure. As odor or gas is generated within the enclosure, it is either adsorbed or absorbed by the blend.

DETAILED DESCRIPTION OF THE INVENTION

Figure 1:
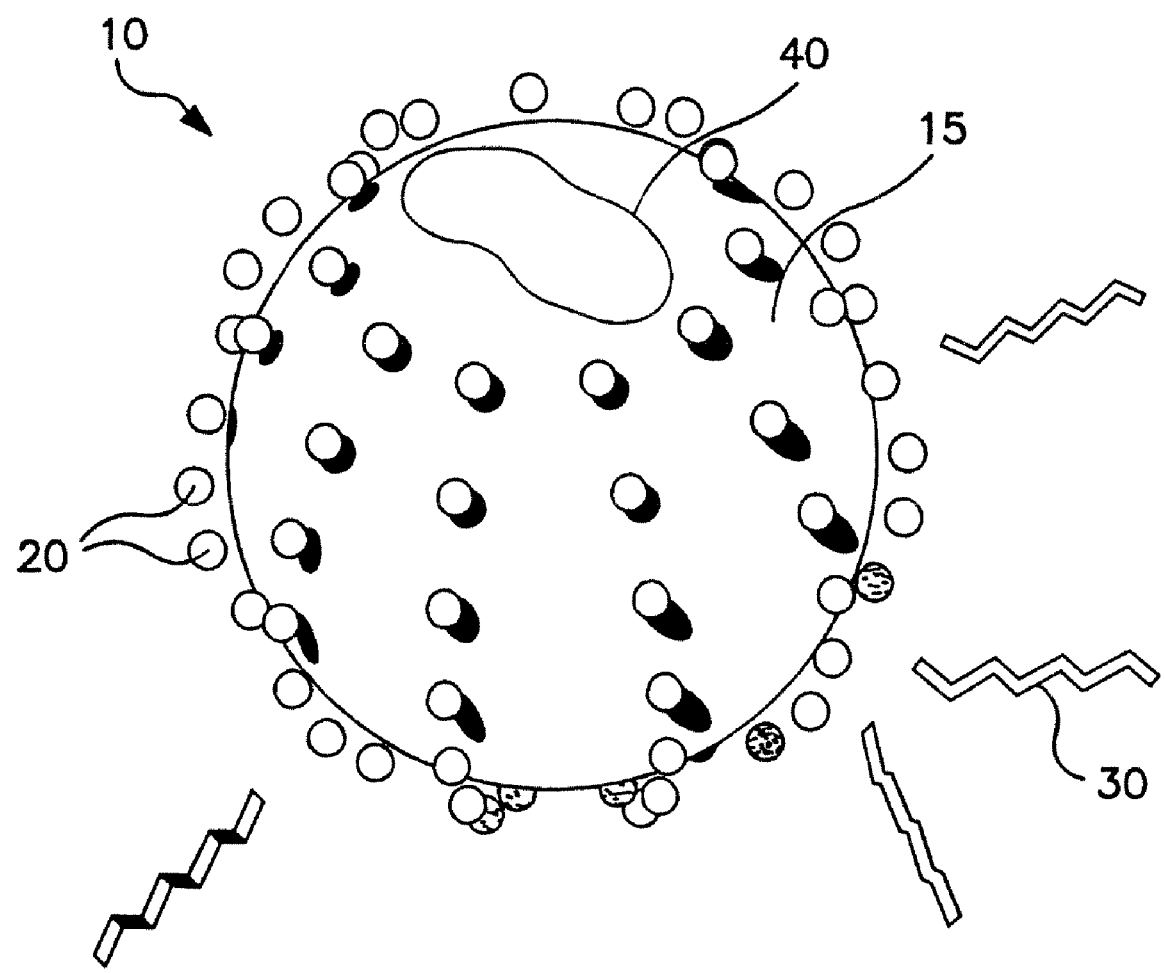
FIG. 1 is a drawing of a modified high surface area material, specifically a nanoparticle of the inventive composition, in accordance with one embodiment of this invention.

No one odor absorbing agent can handle all the chemical components across the many different odorous categories. Therefore, by using a blend of high surface area materials, particularly nanoparticles, and desirably silica nanoparticles in product packaging, various odor causing chemicals can be adsorbed/absorbed on the nanoparticle surfaces, resulting in reduced product odor. In particular, by blending unmodified nanoparticles with metal modified nanoparticles, or alternatively, blending various different metal modified nanoparticles, a targeted odor reducing composition can be formulated. For the purposes of this application, the terms "unmodified" and "nonmodified" are used interchangeably to mean a nanoparticle that has not been modified to have at least one metal component (such as metal ions) associated with it. Also for the purposes of this application, the terms "metal modified" and "metallized" are used interchangeably to mean a nanoparticle that has been modified to have at least one metal component (such as metal ion) associated with it. By being "associated" the metal component is in close proximity to the nanoparticle such as through charge attraction or other more secure bonding methods. In a desirable embodiment, such metal component is not easily dislodged from its association with the nanoparticle.

Often, product odors are not caused by single odor causing chemicals, but instead are caused by combinations of multiple odor causing chemicals. Therefore, by using a blend combination of different modified metallized nanoparticles and/or metallized nanoparticles and unmodified nanoparticles, targeted odor reduction can be achieved for specific product applications. For example, the metal modified nanoparticles would be effective for neutralizing bathroom odors (sulfides and amines) whereas, unmodified nanoparticles would be more effective for neutralizing tobacco odor (aliphatic acids and aldehydes). Further still, a blend of modified and unmodified nanoparticles would be a desirable composition for cooking food (kitchen) odors (aldehydes, sulfides and amines). Such blends may be essentially used to optimize removal of unwanted odors entrapped within a product packaging or in a surrounding environment.

By reacting various transition metals onto the surface of the nanoparticles, the affinity for adsorbing various odor causing chemicals can be changed. The blended nanoparticles may then be added to the product packaging, either as an insert, as part of a product structure, or as part of the inside of the packaging itself (packaging structure), to eliminate or reduce incidence of perceived headspace odor upon opening a product packaging.

In particular, with the addition of tissue manufacturing chemistry into tissue and paper products for the ultimate purposes of providing improved strength, softness and other attributes to the tissue products, there are often odors associated with the chemistry that can build up within the headspace of a product packaging, that result in a negative consumer impression upon opening the product. This build up of odors is most evident upon opening a new package, but may also occur upon the opening of resealable product packaging. These odors may also result from the chemistry of the polymer packaging itself, the glues which are utilized in making the packaging or final product for the consumer, the product itself and any plasticizing agents that may have been employed during product manufacture, or treatments that have been applied to the product. Such build up of odor may occur for example in a bathroom tissue (toilet tissue) package following tissue manufacture and packaging. In this regard, it has been found that the use of blended high surface area materials, and in particular, nanoparticles, applied to either an insert within the package, the product within the package or to the inside of the package itself, assists in reducing the perceived odors which are encountered upon opening a paper product package. Such odor removing compositions can be added to for example bath, facial, towel, toilet or other tissue containing packages having a space (headspace) for accumulation of odor, in order to remove/reduce such odors. It should be recognized that while such odor removing compositions are desirably used in conjunction with rolled paper product packaging (such as bathroom tissue or paper towels), such odor removing compositions may also be used in the packaging of other more durable goods, such as but not limited to, shoes storage cases (i.e. shoe boxes), polymeric containers, and luggage. While the blends of this invention may be used in a wide variety of packages containing goods, the blends of the invention are desirably useful in packaging material that entraps gases or odors (i.e. a packaging material that would not provide sufficient breathability to allow the passage of malodors on its own). Such packaging materials include films, coated papers, cardboard, and tight knit woven materials, as well as certain tightly formed nonwoven materials.

In a desirable embodiment, this invention specifically relates to high surface area materials, such as nanoparticles, which have been modified with at least one metal ion. Blends of the differently modified nanoparticles, or modified nanoparticles and unmodified particles may then be used to adsorb odors in product packaging headspace. It has been discovered that the modified high surface area materials of this invention are particularly useful in removing certain gaseous compounds and/or odorous compounds, while the unmodified high surface area materials are useful in removing other gaseous or odorous compounds.

For the purposes of this application, the terms "gaseous compound" or "gas" includes any molecule or compound that can exist as a gas or vapor. For the purposes of this application, the terms "odorous compound" or "odor" refers to any molecule or compound detectable to the olfactory system. Odorous compounds can exist as a gaseous compound and can also be present in other media such as liquid. The odors may also volatilize from the product over time, upon exposure to heat, light or other environmental conditions.

The blend of such high surface area materials of this invention have at least one high surface area material having a metal component (such as a metal ion) present on the material surface. The metal component creates an active site that binds with at least one gaseous compound and/or odorous compound, thereby entrapping the compound, effectively removing it from the surrounding environment. High surface area materials can also absorb certain gaseous compounds and/or odorous compounds from the surrounding environment by adsorption directly onto the surface area of the high surface area materials themselves. Therefore, as previously indicated, the blend may include either unmodified and modified materials or alternatively a variety of differently modified materials, or a combination thereof.

High surface area materials useful in this invention have a large surface area due to the small size of the individual particles of the high surface area material. High surface area materials useful in this invention have a suitable surface area of at least about 200 square meters/gram, more suitably at least about 500 square meters/gram, and even more suitably at least about 800 square meters/gram.

As previously indicated, "nanoparticles" are examples of high surface area materials useful in this invention. For the purposes of this application, the term "nanoparticle" refers to a high surface material having an effective particle diameter of less than about 500 nanometers. While the invention will be described hereinafter with particular reference to nanoparticles, it will be understood that the invention is useful with various high surface area materials.

FIG. 1 shows a modified nanoparticle 10 according to one embodiment of this invention, useful as a gas and/or odor removing particle. The modified nanoparticle 10 includes a nanoparticle 15 and metal ions 20. While FIG. 1 shows a plurality of metal ions 20, modified nanoparticle 10 can have various amounts of metal ions 20 and will have at least one metal ion 20. The modified nanoparticle 10 is useful for removing various gaseous compounds and/or odorous compounds. The specific compound to be removed is generally dependent on the specific metal ions 20 used and the type of nanoparticle 15. The modified nanoparticle may adsorb odors or gas by attraction of odor or gas materials 30 to the metal ions, or alternatively, directly to the surface of the nanoparticle 40.

Nanoparticles useful in this invention include, without limitation, silica, alumina, magnesium oxide, titanium dioxide, iron oxide, gold, zinc oxide, copper oxide, organic nanoparticles such as polystyrene, and combinations thereof. Nanoparticles are not generally ionic yet still have an overall electric Zeta Potential. "Zeta Potential" refers to the electrical potential, or electrokinetic potential, that exists across the interface of all solids and liquids. Nanoparticles with either positive or negative Zeta Potentials are known. Naturally occurring chemical reactions on the surface of a nanoparticle result in the Zeta Potential of that nanoparticle. For example, silica nanoparticles are tetrahedral complexes of silicon dioxide molecules. On the surface of the silica particles the silicon dioxide molecules can undergo chemical reactions forming silanol groups (SiOH) the silanol groups reacting with other silanol groups to form siloxane bonds (Si—O—Si bonds). The dehydration reactions of the silanol groups to form the silanol bond and the reverse reactions result in a negative Zeta Potential and allow positively charged metal ions to adsorb onto the silica. Such metal ions are therefore closely associated with the silica nanoparticles, not easily removed from such particles.

The nanoparticles useful in this invention will typically have a first Zeta Potential and a second Zeta Potential after adsorption of the metal ion onto the nanoparticle due to the addition of the oppositely-charged metal ions. The Zeta Potential change of the nanoparticle is related to the amount of metal ions adsorbed onto the nanoparticle. This relationship provides a measurement for determining the amount of adsorbed metal ions and a method for controlling the amount of adsorption. For instance, the addition of a dilute solution of copper chloride drop-wise to a silica nanoparticle solution until the Zeta Potential of the silica suspension changed from −25 millivolts to a higher Zeta Potential, such as in the range of about −5 millivolts to −15 millivolts, was found to be provide a sufficient concentration of metal ions adsorbed onto the nanoparticles to remove particular odorous compounds. In one embodiment of this invention the nanoparticle has a difference between the first and second Zeta Potential of at least about 1.0 millivolt and suitably at least about 5.0 millivolts.

The modified nanoparticles of this invention are modified in one embodiment with metal ions that ionically bond with compounds such as gases and odorous compounds. "Metal ion" refers to salt ions and/or ion complexes/complexes of transition metal elements designated as IB through VIIIB on the periodic table. Other ions can be used in the invention as well. Metal ions are adsorbed onto the high surface area materials due to differences in electric potential. Positively charged metal ions are adsorbed onto a negatively charged surface of a nanoparticle and vice versa. Examples of metal ions useful in this invention include, without limitation, copper ion ($Cu^{+2}$), silver ion ($Ag^{+1}$), gold ion ($Au^{+1}$ and $Au^{+3}$), iron (II) ion ($Fe^{+2}$), and iron (III) ion ($Fe^{+3}$) and combinations thereof.

In one embodiment of this invention a modified nanoparticle useful in this invention has a negative Zeta Potential and adsorbs positively charged metal ions. One suitable modified nanoparticle has a negative Zeta Potential of about −1 to −50 millivolts and suitably about −1 to −20 millivolts. In one embodiment of this invention the modified nanoparticle having a negative Zeta Potential is a silica nanoparticle. Silica nanoparticles useful in this invention are available from Nissan Chemical Industries, Ltd., Houston, Tex., under the name SNOWTEX, and have a particle size range of about 1-100 nanometers. The silica nanoparticles can be modified with a positively charged metal ion such as copper ions, silver ions, gold ions, iron ions, and combinations thereof.

In another embodiment of this invention the modified nanoparticle useful in this invention has a positive Zeta Potential and adsorbs negatively charged metal ion complexes. One suitable modified nanoparticle has a positive first Zeta Potential of about 1 to 70 millivolts and suitably about 10 to 40 millivolts. In one embodiment of this invention the modified nanoparticle having a positive Zeta Potential is an alumina nanoparticle. Alumina nanoparticles are also available from Nissan Chemical Industries, Ltd., Houston, Tex., under the name ALUMINASOL, and SNOWTEX-AK (Alumina coated silica) and have size ranges of about 1-300 nanometers. The alumina nanoparticles can adsorb negatively charged metal complexes such as permanganate ($MnO_4^{-1}$).

In an alternative embodiment of the invention, the modified nanoparticles can include metal components that are associated with them, but which association is not entirely reliant on charge differentials as with the ionic bonding described above. For instance, it is also possible to bond metal and silica particles to form a "coordinate" and/or "covalent bond." This may have a variety of benefits, such as reducing the likelihood that any of the metal will remain/become free during use (e.g., after washing). Strong adherence of the metal to the silica particles also optimizes odor adsorption effectiveness.

Numerous techniques may be utilized to form a stronger bond between the transition metal and nanoparticles. Silica sols, for example, are generally considered stable at a pH of greater than about 7, and particularly between a pH of 9-10. When dissolved in water, salts of transition metals are acidic (e.g., copper chloride has a pH of approximately 4.8). Thus, when such an acidic transition metal salt is mixed with a basic silica sol, the pH is lowered and the metal salt precipitates on the surface of the silica particles. This compromises the stability of the silica particles. Further, at lower pH values, the number of silanol groups present on the surface of the silica particles is reduced. Because the transition metal binds to these silanol groups, the capacity of the particles for the transition metal is lowered at lower pH values. In order to ameliorate the pH-lowering affect caused by the addition of an acidic transition metal salt (e.g., copper chloride), certain embodiments of the present invention can employ selective control over the pH of the silica particles during mixing with the transition metal. The selective control over pH may be accomplished using any of a variety of well-known buffering systems known in the art.

Other techniques may also be utilized to further enhance the strength of the bonds formed between the transition metal and the silica particles. Coupling agents in an effective amount may be used to link the transition metal to the silica particle, for example. Such coupling agents may be employed with or without the pH adjustment discussed above. In some cases, an organofunctional silane coupling agent may be used to link the transition metal to the silica particles. Some examples of suitable organofunctional silane coupling agents that may be used include, but are not limited to, vinyltrichlorosilane, vinyltrimethoxysilane, vinyltriethoxysilane, vinylmethyidichlorosilane, vinylmethyldimethoxysilane, vinylm- ethyldiethoxysilane, 5-hexenyltrimethoxysilane, 3-glycidoxypropyltrimethoxysilane, 3-glycidoxypropyltriethoxysilane, 3-glycidoxypropylmethyldimethoxysilane, 3-glycidoxypropylmethyidiethoxysilane, 3-(meth)acryloxypropyltrimethoxysilane, 3-(meth)acryloxypropyltriethoxysilane, 3-(meth)acryloxypropylmethyldimethoxysilane, 3-(meth)acryloxypropylmethyldiethoxysilane, 4-vinylphenyltrimethoxysilane, 3-(4-vinylphenyl)propyltrimethoxysilane, 4-vinylphenylmethyltrimethoxysilane, 3-aminopropyltrimethoxysilane, 3-aminopropyltriethoxysilane, 3-aminopropylmethyidimethoxysilane, 3-aminopropylmethyldiethoxysilane, 3-(2-aminoethyl)aminopropyltrimethoxysilane, 3-mercaptopropyltrimethoxysilane, 3-mercaptopropyltriethoxysilane, 3-mercaptopropylmethyidimethoxysilane, 3-mercaptopropylmethyldiethoxysilane, and partial hydrolyzates thereof. Of these coupling agents, organofunctional alkoxysilanes, and particularly aminofunctional alkoxysilanes (e.g., 3-aminopropyltriethyoxysilane), are desirable. Generally speaking, the silane coupling agents may be covalently linked to the silica particles through the silanol groups (Si—OH) present on the surface thereof. Specifically, the silicon atom of the silane coupling agent may form a covalent bond with the oxygen of the silanol group. Once the silane coupling agent is covalently linked to the silica particles, the organofunctional group may form a coordinate bond with the transition metal. Copper, for example, may form a coordinate bond with different amino groups present on aminopropyltriethoxysilane coupling agents. Such alternative bonding is further described in Ser. No. 10/686,938 filed Oct. 16, 2003, titled Method For Reducing Odor Using Metal-Modified Silica Particles, and in the names of Bao T. Do et al. under Express Mailing Number EV 342689978 US and such Application is hereby incorporated by reference in its entirety.

The unmodified nanoparticles are merely the previously described nanoparticle materials without the addition of metal components along their surfaces. The unmodified nanoparticles may have predispositions themselves to the adsorption of particular odors. For instance, in blending such materials, the predisposition of unmodified alumina particles to adsorb acid-based odors/gases and the predisposition of silica nanoparticles to adsorb aldehyde-based odors/gases is desirably considered. Unmodified nanoparticles are further described in described in Ser. No. 10/686,933 filed Oct. 16, 2003, titled Method For Reducing Odor Using Colloidal Particles, and in the names of John Gavin MacDonald et al. under Express Mailing Number EV 342689964 US and such Application is hereby incorporated by reference in its entirety.

Current odor control materials such as activated charcoal or sodium bicarbonate rely on the surface area to absorb certain odors. Using these materials is not as effective at odor removal than the modified high surface area materials of this invention. The addition of a metal ion adsorbed onto the surface of a nanoparticle, as in this invention, provides an active site for capturing and neutralizing gases and odorous compounds. In addition, the modified nanoparticles of this invention still have the large surface area that is useful in absorbing other odorous compounds. The metal component active sites of the modified nanoparticles are particularly useful in removing odorous compound such as mercaptans, ammonia, amines, and mono- and di-sulfides. Other odorous compounds such as aliphatic ketones, carboxylic acids, aliphatic aldehydes, and aliphatic terpenoids can be removed by adsorption onto the large surface area of the nanoparticles. Modified nanoparticles are useful in removing odors caused by sulfides, disulfides, trisulfides, thiols, mercaptans, ammonia, amines, isovaleric acid, acetic acid, propionic acid, hexanal, heptanal, 2-butanone, 2-pentanone, 4-heptanone, and combinations thereof. Modified nanoparticles can also remove gases such as ethylene gas, carvone, dienals, and terpenoids.

More than one type of metal ion can be coated onto a single nanoparticle or multiple nanoparticles. This has an advantage in that certain metal ions may be better at removing specific gases and/or odorous compounds than other metal ions even on individual nanoparticles. In one embodiment of this invention, more than one type of metal ion are adsorbed onto different nanoparticles that are then blended together, for removing at least two gaseous compounds or odorous compounds from an environment. In this fashion, modified nanoparticles of this invention can be used in combination with other modified nanoparticles for efficient (or targeted) removal of various gases and odors.

For instance, In one embodiment of this invention copper ion modified silica nanoparticles are used in combination with permanganate ion modified magnesium oxide nanoparticles. By using the two different modified nanoparticles in combination, numerous odorous compounds can be removed. For example, the modified silica nanoparticle is useful for removing sulphur and amine odors and the modified magnesium oxide nanoparticle is useful in removing carboxylic acid odors. Combining modified nanoparticles of this invention therefore allows for removal of a broader range of odors.

In a second embodiment, the modified nanoparticles as previously described, may be combined with the unmodified nanoparticles for a broad range of adorption options. For instance, in one embodiment, at least one type of modified nanoparticle is blended with at least one type of unmodified nanoparticle. In still another alternative embodiment, at least two types of modified nanoparticles are blended with at least one type of unmodified nanoparticle.

Typically, the nanoparticles described are in either colloidal form or suspensions. "Colloidal" nanoparticles refer to nanoparticles that may exist as a stable liquid dispersion. The nanoparticles of the present invention may possess various forms, shapes, and sizes depending upon the desired result. For instance, the nanoparticles may be in the shape of a sphere, crystal, rod, disk, tube, string, etc. The average size of the nanoparticles is generally less than about 100 nanometers, in some embodiments from about 1 to about 50 nanometers, in some embodiments from about 2 to about 50 nanometers, and in some embodiments, from about 4 to about 20 nanometers. As used herein, the average size of a particle refers to its average length, width, height, and/or diameter.

The nanoparticles may have a surface area of from about 50 square meters per gram ($m^2/g$) to about 1000 $m^2/g$, in some embodiments from about 100 $m^2/g$ to about 600 $m^2/g$, and in some embodiments, from about 180 $m^2/g$ to about 240 $m^2/g$. Surface area may be determined by the physical gas adsorption (B.E.T.) method of Bruanauer, Emmet, and Teller, Journal of American Chemical Society, Vol. 60, 1938, p. 309, with nitrogen as the adsorption gas. In addition, the nanoparticles may also be relatively nonporous or solid. That is, the nanoparticles may have a pore volume that is less than about 0.5 milliliters per gram (ml/g), in some embodiments less than about 0.4 milliliters per gram, in some embodiments less than about 0.3 ml/g, and in some embodiments, from about 0.2 ml/g to about 0.3 ml/g. Without intending to be limited by theory, it is believed that nanoparticles having such a small size and high surface area may improve the adsorption capability of the nanoparticles for many odorous compounds. Moreover, it is believed that the solid nature, i.e., low pore volume, of the nanoparticles may enhance the uniformity and stability of the nanoparticles, without sacrificing its odor adsorption characteristics.

As previously stated, the nanoparticles may be formed from a variety of materials, including, but not limited to, silica, alumina, zirconia, magnesium oxide, titanium dioxide, iron oxide, zinc oxide, copper oxide, organic compounds such as polystyrene, and combinations thereof. For example, alumina nanoparticles may be used for odor reduction in accordance with the present invention. Some suitable alumina nanoparticles are described in U.S. Pat. No. 5,407,600 to Ando, et al., which is incorporated herein in its entirety by reference thereto for all purposes. Further, examples of commercially available alumina nanoparticles include, for instance, ALUMINASOL 100, ALUMINASOL 200, and ALUMINASOL 520, which are available from Nissan Chemical Industries Ltd. Alternatively, silica nanoparticles may be utilized, such as SNOWTEX-C, SNOWTEX-O, SNOWTEX-PS, and SNOWTEX-OXS, which are also available from Nissan Chemical. SNOWTEX-OXS particles, for instance, have a particle size of from 4 to 6 nanometers, and may be ground into a powder having a surface area of approximately 509 square meters per gram. Also, alumina-coated silica particles may be used, such as SNOWTEX-AK available from Nissan Chemical.

The nanoparticles, such as referenced above, may possess units that may or may not be joined together. Whether or not such units are joined generally depends on the conditions of polymerization. For instance, when forming silica nanoparticles, the acidification of a silicate solution may yield $Si(OH)_4$. If the pH of this solution is reduced below 7 or if a salt is added, then the units may tend to fuse together in chains and form a "silica gel." On the other hand, if the pH is kept at a neutral pH or above 7, the units may tend to separate and gradually grow to form a "silica sol." Such silica nanoparticles may generally be formed according to any of a variety of techniques well known in the art, such as dialysis, electrodialysis, peptization, acid neutralization, and ion exchange. Some examples of such techniques are described, for instance, in U.S. Pat. No. 5,100,581 to Watanabe, et al.; U.S. Pat. No. 5,196,177 to Watanabe, et al.; U.S. Pat. No. 5,230,953 to Tsugeno, et al. and U.S. Pat. No. 5,985,229 to Yamada, et al., which are incorporated herein in their entirety by reference thereto for all purposes.

In one particular embodiment, a silica nanoparticle sol is formed using an ion-exchange technique. For exemplary purposes only, one such ion-exchange technique will now be described in more detail. Initially, an alkali metal silicate is provided that has a molar ratio of silicon ($SiO_2$) to alkali metals ($M_2O$) of from about 0.5 to about 4.5. For instance, sodium water glass may be utilized that has a molar ratio of from about 2 to about 4. An aqueous solution of the alkali metal silicate is obtained by dissolving it in water at a concentration of, for instance, from about 2 wt. % to about 6 wt. %. The alkali metal silicate-containing aqueous solution may then be contacted with one or more ion-exchange resins. For instance, the solution may first be contacted with a strong-acid to ion-exchange all the metal ions in the aqueous solution. Examples of such strong acids include, but are not limited to, hydrochloric acid, nitric acid, sulfuric acid, and so forth. The contact may be accomplished by passing the aqueous solution through a column filled with the strong acid at a temperature of from about 0° C. to about 60° C., and in some embodiments, from about 5° C. to about 50° C. After passing through the column, the resulting silicic acid-containing aqueous solution may have a pH value of from about 2 to about 4. If desired, another strong acid may be added to the silicic acid-containing aqueous solution to convert the impurity metal components into dissociated ions. This additional strong acid may decrease the pH value of the resulting solution to less than about 2, and in some embodiments, from about 0.5 to about 1.8.

The metal ions and the anions from the strong acid may be removed from the solution by consecutive application of a strong acid (i.e., cation-exchange resin) and strong base (anion-exchange resin). Examples of suitable strong bases include, but are not limited to, sodium hydroxide, potassium hydroxide, and so forth. As a result of this consecutive application, the silicic acid-containing aqueous solution may have a pH value of from about 2 to about 5. This acidic aqueous solution may then be contacted with one or more additional strong bases to stabilize the solution at a pH value of from about 7 to about 9.

The stabilized silicic acid-containing aqueous solution is then fed to a container in which the liquid temperature is maintained at from about 70° C. to about 100° C. This process results in an increase in concentration of the silica to from about 30 wt. % to about 50 wt. %. The stable aqueous silica sol may then be consecutively contacted with a strong acid and strong base, such as described above, so that the resulting aqueous silica sol is substantially free from polyvalent metal oxides, other than silica. Finally, ammonia may be added to the aqueous sol to further increase its pH value to from about 8 to about 10.5, thereby forming a stable aqueous silica sol having a silica concentration of from about 30 wt. % to about 50 wt. %, a mean particle size of from about 10 to about 30 nanometers, and that is substantially free from any polyvalent metal oxides, other than silica.

Modified nanoparticles are made from unmodified nanoparticles by several methodologies. In one desirable method, they are made by mixing unmodified nanoparticles with solutions containing metal ions. Such solutions are generally made by dissolving metallic compounds into a solvent resulting in free metal ions in the solution. The metal ions are drawn to and adsorbed onto the nanoparticles due to the electric potential differences. The Zeta Potential of a nanoparticle changes after the adsorption of metal ions according to this invention. Thus the Zeta Potential can be used to monitor the adsorption of metal ions onto the nanoparticle. The formation of such modified nanoparticles is described in detail in U.S. patent application Ser. No. 10/137,052 entitled Metal Ion Modified High Surface Area Materials for Odor Removal and Control, filed Apr. 30, 2002 to John Gavin MacDonald, which is incorporated by reference hereto in its entirety.

Unmodified and modified high surface area material blends according to this invention are versatile and can be used alone or in combination with other odor reducing/masking tools, for effective odor removal and control. Unlike activated charcoal deodorants, the unmodified and modified nanoparticle blends of this invention maintain their odor neutralizing effects in solution. It should be recognized that use of the phrase unmodified and modified nanoparticle blend is meant to encompass either blends of modified and unmodified high surface area materials, blends of differently modified high surface area materials, blends of different unmodified high surface area materials or combinations of each. The unmodified and modified nanoparticle blends of this invention also maintain odor neutralizing properties when dry and in aerosol form. This versatility allows for uses in various commercial product applications. Other advantages of the unmodified and modified nanoparticle blends are that they are colorless in solution and white in powder form (activated charcoal is typically black).

As previously stated, the unmodified and modified nanoparticle blends can be used to reduce/eliminate headspace odor from product packaging. For instance, the unmodified and modified nanoparticle blends of this invention can be applied to various materials for insertion into product packaging. In one embodiment of this invention the unmodified and modified nanoparticle blends are held onto a surface of a material for insert, by the electrical potential differences between the unmodified and modified nanoparticle blends (Zeta Potential) and the material surface (Streaming Potential).

As an example, the unmodified and modified nanoparticle blends of this invention can be applied as a solution to a surface and dried, resulting in a surface that absorbs gas and/or odors. In one embodiment of this invention the unmodified and modified nanoparticle blends are coated onto inserts to be placed inside product packaging. Such inserts may be of fabric, film or fibrous based construction. For instance, such inserts may be constructed from woven or nonwoven fabric materials. When utilized, the nonwoven fabrics may include, but are not limited to, spunbonded webs (apertured or non-apertured), meltblown webs, bonded carded webs, air-laid webs, coform webs, hydraulically entangled webs, and the like. In an alternative embodiment, such inserts may be produced from injection molded polymers. In a further alternative embodiment, such inserts may be crystalline and/or amorphous polymers such as a polymer wafer (for example a packing "peanut"). In still another alternative embodiment, such insert may be produced from other more durable materials, such as wood, ceramic, metallic or glass inserts, depending on the nature of the product that is contained within the product packaging.

The amount of the nanoparticles present on the insert may vary depending on the nature of the insert and its intended application. In some embodiments, for example, the dry, solids add-on level is from about 0.001% to about 20%, in some embodiments from about 0.01% to about 10%, and in some embodiments, from about 0.1% to about 4%. The "solids add-on level" is determined by subtracting the weight of the untreated insert from the weight of the treated insert (after drying), dividing this calculated weight by the weight of the untreated insert, and then multiplying by 100. Higher add-on levels may provide optimum odor reduction.

The nanoparticles may be applied to an insert using any of a variety of well-known application techniques. Suitable techniques for applying the blend composition to an insert include printing, dipping, spraying, melt extruding, solvent coating, powder coating, and so forth. The nanoparticles may be incorporated within the matrix of the insert and/or applied to the surface thereof. For example, in one embodiment, the nanoparticles are coated onto one or more surfaces of the insert. When coated onto the insert, the resulting thickness of the coating may be minimal so that it is almost invisible to the naked eye. For instance, the thickness of the coating may be less than about 1 micron, in some embodiments from about 2 to about 500 nanometers, and in some embodiments, from about 4 to about 200 nanometers.

The percent coverage of the nanoparticles on the surface of the insert may be selected to achieve the desired odor reduction. Typically, the percent coverage is greater than about 50%, in some embodiments greater than about 80%, and in some embodiments, approximately 100% of the area of a given surface.

In another alternative embodiment, such insert may be placed (such as adhesively applied) on the inside surface of a product packaging. Alternatively, the nanoparticle blend may be coated onto a portion of the inside surface of the product packaging itself, and especially a portion of the inside surface that would not likely be exposed to product abrasion during product transport or sale. For instance, such blend application could be to the inside surface of a product package contained in the headspace area which is not in contact with the product. In still another alternative embodiment of this invention, the nanoparticle blend may be placed/coated on a portion of a product itself to be contained in the product packaging, but that would not be worn off during product transport or use. For instance, the blend may be placed on the outer tissue layer (s) of the product. However, it is desirable that if the nanoparticle blend is placed on a product itself, it is placed in such a location that it does not impact a consumer's ultimate use of the product.

Unmodified and modified nanoparticle blends can be coated in various amounts depending on need. Suitably, unmodified and modified nanoparticle blends are coated on fabrics, films, or fibers in an amount of about 0.001 to 10.0 grams per square meter and more suitably about 0.1 grams per square meter.

Figure 2:
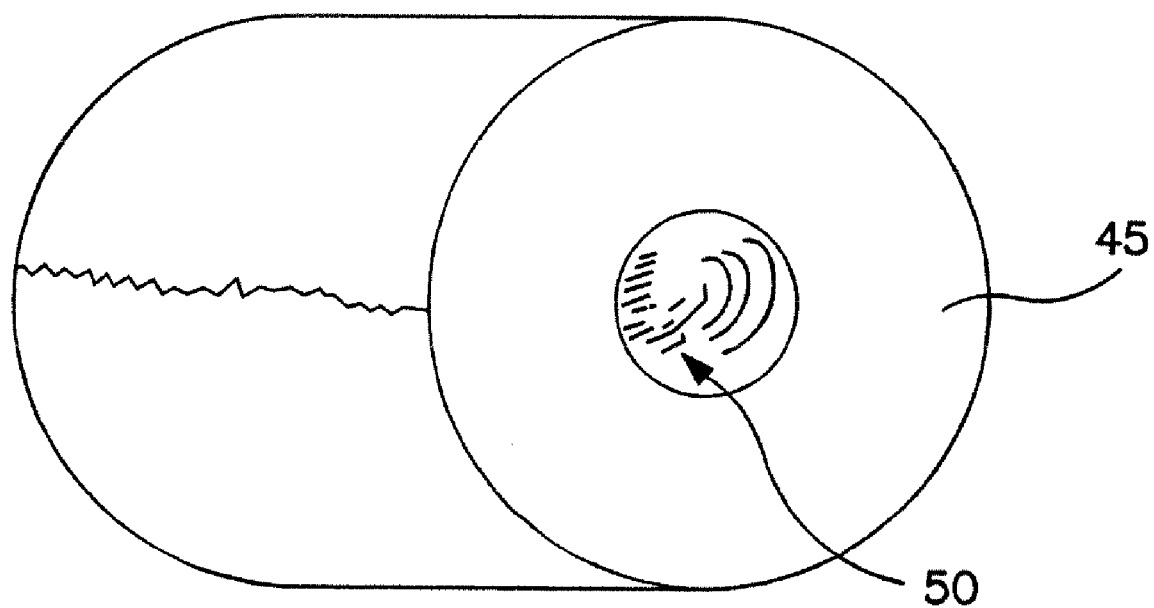
FIG. 2 is a perspective drawing of one use of an inventive composition in accordance with one embodiment of this invention, and in particular, a bathroom tissue roll.
Figure 3:
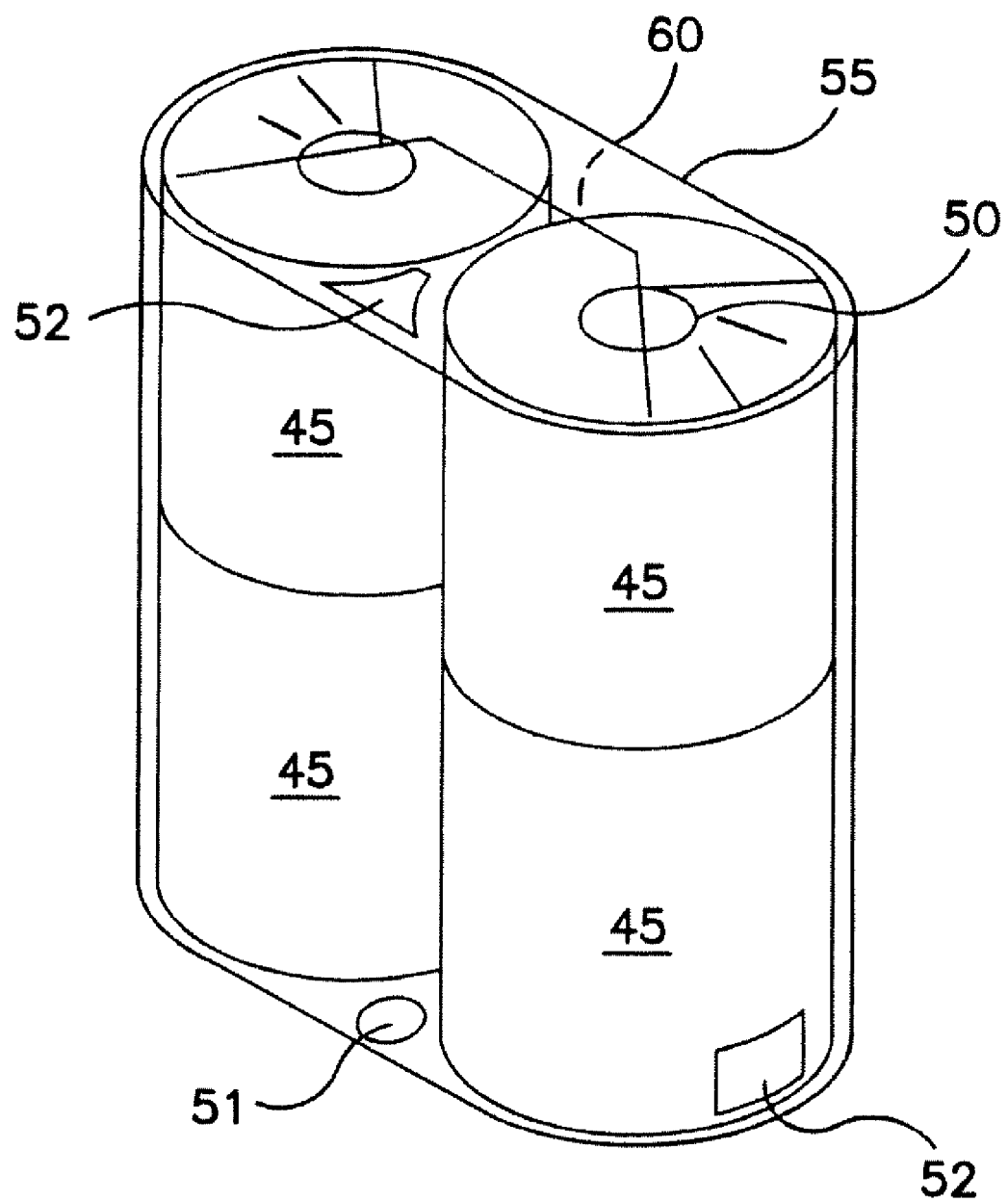
FIG. 3 is a perspective drawing of bathroom tissue packaging including the various placement of the inventive composition.

In a desirable embodiment, a nanoparticle blend is directly associated with a tissue product by being applied to the paper rolls (core) which support toilet/bathroom tissue in packaging. As can be seen in FIG. 2, which illustrates a perspective view of a bathroom tissue roll 45 including a hollow, cylindrical cardboard core 50, a blend of different metal modified silica nanoparticles have been applied as a coating to the inside surface of the roll core 50. Such nanoparticles may be applied prior to bathroom tissue packaging (during manufacture), such as while the core is being assembled with the tissue, or alternatively, during placement of the rolls within their final packaging, such as in the polymeric film packaging. The rolls 45 are wrapped (i.e enclosed) in packaging 55, as can be seen in FIG. 3. Desirably, in certain embodiments, such packaging is sealed so as to maintain some environment within the package and to eliminate or limit exposure of the product to humidity and other external environmental conditions. In this fashion, any odor which accumulates in the headspace 60 between the rolls 45 and packaging 55, can be adsorbed by the nanoparticle blends of the inventive composition. As can be seen in FIG. 3, the blends of nanoparticles can be positioned on a disc insert 51 contained in the package, on an inside surface 52 of the product package itself, or alternatively, on a portion of the product 50, contained within the package.

In an alternate embodiment, the nanoparticle blends can be added to the core, insert or packaging in conjunction with additional chemistries to absorb odor. For instance, such particles may be added with activated carbon, diatomaceous earth, baking soda, zeolites, ceramics, glass wool, clay, resins or other odor absorbent chemical. In still another alternative embodiment, a masking chemical agent may be added to the core, insert or packaging along with such blended nanoparticles.

It should therefore be recognized that methods for removing odor from a product packaging (and the headspace of a product packaging) include the steps of formulating a blend of either differently modified high surface area materials or modified high surface area materials and unmodified high surface area materials, and applying such formulated blend to the inside of a product packaging. Desirably the product packaging is then sealed so as to maintain a relatively closed environment inside the packaging. In one embodiment, the application of the formulated blend is applied by coating the blend onto either the product packaging inside surface itself, an insert contained within the product packaging, or a portion of the product contained within the product packaging.

The unmodified and modified nanoparticle blends are exemplified by the following demonstrated nanoparticle/odor affinities and the following product example. Each of the formulated nanoparticle types can be blended in either dry or wet form following formation, prior to blend application. It is desirable that such blends be achieved in one of two ways. The blends may be accomplished by mixing water suspensions of at least two different modified nanoparticles with stirring, or alternatively mixing water suspensions of modified nanoparticles with unmodified nanoparticles. The mixtures can then be applied to a desired substrate. Alternatively, the desired substrate can be treated/coated with a first nanoparticle suspension and then treated/coated with a second nanoparticle suspension. While the examples are meant to further describe the inventive compositions and product configurations, they are not meant to be limiting.

Nanoparticle Affinities

In evaluating the affinities of unmodified and modified nanoparticles for adsorbing particular odors/gases, testing was conducted on the nanoparticles and odors/gases in question. Testing was in accordance with the following procedure:
Test Methods:

Gas Chromatography (GC) Headspace Test Method:

Odor absorption was determined using headspace gas chromatography testing conducted on an Agilent Technologies 5890, Series II gas chromatograph with an Agilent Technology 7694 headspace sampler, both available from Agilent Technologies, Waldbronn, Germany. Helium was used as the carrier gas (injection port pressure: 12.7 psig (188.9 kPa); headspace vial pressure: 15.8 psig (210.3 kPa); supply line pressure: 60 psig (515.1 kPa)). A DB-624 column that had a length of 30 m and an internal diameter of 0.25 mm was used for the odorous compound (available from J&W Scientific, Inc. of Folsom, Calif.).

The operating parameters used for the headspace gas chromatography are shown below in Table 1.

TABLE 1

Operating Parameters for the Headspace Gas Chromatography Device
Headspace Parameters

| | | |
|---|---|---|
| Zone Temps, ° C. | Oven | 37 |
| | Loop | 42 |
| | TR. Line | 47 |
| Event Time, minutes | GC Cycle time | 10.0 |
| | Vial eq. Time | 10.0 |
| | Pressuriz. Time | 0.20 |
| | Loop fill time | 0.20 |
| | Loop eq. Time | 0.15 |
| | Inject time | 0.30 |
| Vial Parameters | First vial | 1 |
| | Last vial | 1 |
| | Shake | [off] |

The test procedure involved placing 0.005-0.006 g of a sample containing the odor absorbing agent in a 20 cubic centimeter (cc) headspace vial. Using a syringe, an aliquot of the odorous compound was also placed in the vial. The vial was then sealed with a cap and a septum and placed in a headspace gas chromatography oven at 37° C. After ten minutes, a hollow needle was inserted through the septum and into the vial. A 1 cc sample of the headspace (air inside the vial) was then injected into the gas chromatograph.

Initially, a control vial with only the aliquot of odorous compound was tested to define 0% odorous compound adsorption. To calculate the amount of headspace odorous compound removed by the sample, the peak area for the odorous compound from the vial with the sample was compared to the peak area from the odorous compound control vial. Testing was initially done with 5 µl of 2,3-butanedione, 5 µl of acetaldehyde, and 5 µl of 3-methyl butanal. Each sample was tested in duplicate. Testing was done on additional materials as noted below.

Solid Phase MicroExtraction (SPME) Test Method

This method is commonly used to collect and analyze volatile components of products or odors or air pollution as described in *Application of a SPME method for the Rapid Determination of VOC's*. A. Bene, J-L. Luisier and A. Formage. Chimia. 56, 289-291 (2002). It uses a specialized fiber (85 micron Carboxen/PDMS StableFlex fiber assembly (Supelco, Bellefonte, Pa.)) to collect the volatile components over a period of time and then release them into the gas chromatography (GC) inlet port for analysis, and in addition identification, when coupled with a Mass Spectrometer (MS).

With the COTTONELLE® with Aloe and E bath tissue (available from Kimberly-Clark Corporation), the odor was collected by inserting the SPME fiber probe into the package of bathroom tissue (4 pack) for 30 minutes. The SPME fiber was then removed and placed into the intake of the GC unit. The volatiles were then released and analyzed by GC followed by MS. A quantitative measurement of odor causing chemical reduction was determined by comparing the area of the chemical odor component of the control package (no treatment) to that of the nanoparticle treated package. Thus % odor reduction was expressed in this manner.

The data suggests that for optimal odor removal, nanoparticles with the proper metal modification should first be determined, or alternatively, the proper unmodified nanoparticles should be identified. In such a fashion, a blend of appropriate odor reducing nanoparticles may be compiled in accordance with specific product needs. The blending technology offers the versatility of being able to design the correct metal ion type or unmodified type and concentration for the specific target application and odorous compounds.

For example, the chemical composition (content as %) of the target odor in question and also the contribution (%) each chemical has on the overall odor should first be reviewed. The contribution is derived from the concentration of the odorous chemical (in parts per million or billion) versus the human threshold value (lowest concentration that the human nose can detect). By determining this information one can then design the nanoparticle blend that would remove all the chemical components of the odor most efficiently.

An examples for illustration is as follows:
Cat odor can be broken down into the following components:

| Chemical | Measured (ppb) | Threshold (ppb) | Content (%) | Contribution (%) |
|---|---|---|---|---|
| Ammonia | 1980 | 1500 | 98.1 | 0.9 |
| n-Butyric Acid | 2.4 | 0.19 | 1.2 | 87.3 |
| Trimethyl Amine | 0.33 | 0.03 | — | 7.3 |

The designed nanoparticle blend for the cat odor would comprise metal modified nanoparticles (amine odor removal) as the major component with the minor amount being the unmodified alumina nanoparticle (for acid removal). This ratio is due to the amines giving rise to over 98% of the odor content compared to the acid component (900 times less in concentration). The human nose is more sensitive to the acid odor and hence the contribution of the acid is higher. One would only require a small amount (100 times less) of the alumina nanoparticles in the blend in order to remove the low concentration (2.4 ppb) of the acid odor.

In the second example one can design a very specific odor absorbing nanoparticle blend that would work on removing sock odor.

Sock odor can be broken down into the following components:

| ODOR | Threshold (ppb) | Measured (ppb) | Content (%) | Contribution (%) |
|---|---|---|---|---|
| Iso-Valeric acid | 0.078 | 1.4 | 15.7 | 65.4 |
| N-Valeric acid | 0.037 | 0.1 | 1.3 | 11.3 |
| Hydrogen Sulfide | 0.41 | 0.7 | 8.1 | 6.4 |

The specific nanoparticle blend would be a mixture of alumina and metal modified silica nanoparticles. The alumina nanoparticles would be in twice the concentration compared to the metal modified silica nanoparticles of the blend. There is twice the acid odor in the "sock odor" as there is sulfide odor.

Unmodified Nanoparticle Affinity for Odor Adsorption Example 1

The effectiveness of the unmodified nanoparticles to adsorb odorous compounds was demonstrated. Three types of silica nanoparticles were tested. Specifically, the silica nanoparticles were SNOWTEX-PS, SNOWTEX-O, and SNOWTEX-C, all of which are commercially available from Nissan Chemical America of Houston, Tex. The particles had an average particle size of between 10 to 20 nanometers, a surface area between 180 to 240 square meters per gram, and were present at approximately 20 wt. % solids in the solution. The SNOWTEX-C suspension was diluted to a 5 wt. % solids solution by adding deionized water while stirring for 10 minutes. The suspension was then poured into a shallow dish. A KIMWIPES® wiper, which is a 1-ply cellulosic tissue wiper available from Kimberly-Clark Corporation, was dipped into the dish and then allowed to air dry on the sash of a fume hood. After drying, the add-on level on nanoparticle solids was approximately 2.4% wt/wt based upon the weight of the tissue.

The samples were then tested for odor adsorption as described above. The results are shown below in Tables 3-4 in terms of milligrams of the odorous compound removed per gram of sample, i.e., relative adsorption efficiency, and percent odor removed.

TABLE 3

Removal of 2,3 Butanedione

| Sample | Relative Adsorption Efficiency (mg odor causing chemical removed/g sample) | % Odor causing chemical removed |
|---|---|---|
| SNOWTEX-C | 372 | 78 |

TABLE 4

Removal of 3-Methyl Butanal

| Sample | Relative Adsorption Efficiency (mg odor causing chemical removed/g sample) | % Odor causing chemical removed |
|---|---|---|
| SNOWTEX-C | 90 | 22 |

The samples were then tested for various odor adsorption as described above. The results are shown below in Tables 5-7 in terms of milligrams of the odorous compound removed per gram of sample, i.e., relative adsorption efficiency, and percent odor removed.

TABLE 5

Removal of Acetaldehyde

| Sample | Relative Adsorption Efficiency (mg odor causing chemical removed/g sample) | % Odor causing chemical removed |
|---|---|---|
| SNOWTEX-PS | 35 | 46 |
| SNOWTEX-O | 36 | 65 |
| SNOWTEX-C | 90 | 22 |

TABLE 6

Removal of 2,3 Butanedione

| Sample | Relative Adsorption Efficiency (mg odor causing chemical removed/g sample) | % Odor causing chemical removed |
|---|---|---|
| SNOWTEX-C | 372 | 78 |

TABLE 7

Removal of 3-Methyl Butanal

| Sample | Relative Adsorption Efficiency (mg odor causing chemical removed/g sample) | % Odor causing chemical removed |
|---|---|---|
| SNOWTEX-C | 90 | 22 |

As indicated, the unmodified silica nanoparticles were capable of effectively adsorbing aldehyde and ketone odors when contained on a fibrous substrate.

Unmodified Nanoparticle Affinity for Odor Adsorption Example 2

The effectiveness of the unmodified nanoparticles to adsorb other malodorous compounds was demonstrated. Two types of nanoparticles were tested. Specifically, the nanoparticles were SNOWTEX-C and SNOWTEX-AK, all of which are commercially available from Nissan Chemical America of Houston, Tex. The particles had an average particle size of between 10 to 20 nanometers, a surface area between 180 to 240 square meters per gram, and were present at approximately 20 wt. % solids in the solution. 10 milliliters of the silica nanoparticles were dried at 80° C. to form powders that were then ground to a surface area of 220 square meters per gram. The powders were coated onto a KIMWIPES® wiper as described in Example 1. After drying, the add-on level was approximately 2% wt/wt based on Tissue.

The samples were then tested for odor adsorption as described above using 1.96 milligrams of pyridine. The results are shown below in Table 8 in terms of milligrams of the odorous compound removed per gram of sample, i.e., relative adsorption efficiency, and percent odor removed.

TABLE 8

Removal of Pyridine

| Sample | Relative Adsorption Efficiency (mg odor causing chemical removed/g sample) | % Odor causing chemical removed |
|---|---|---|
| SNOWTEX-C | 105 | 78 |
| SNOWTEX-AK | 84 | 68 |

As indicated, the unmodified silica nanoparticles were capable of effectively adsorbing the pyridine odor when contained on a substrate.

Modified Nanoparticle Affinity for Odor Adsorption Example 3

A dilute suspension of modified silica nanoparticles was made by adding 1 milliliter of SNOWTEX C, available from Nissan Chemical Industries, Ltd., Houston, Tex., to 9 milliliters of deionized water. The suspension was pipetted in equal portions into four cuvets. Solutions of 0.01 percent by weight of each of copper chloride ($CuCl_2$), silver nitrate ($AgNO_3$), and zinc chloride ($ZnCl_2$), all from Aldrich Chemical Company, Milwaukee, Wis., were prepared and one drop of each was added to a separate cuvet. The Zeta Potential of all four suspension was then measured by a Zetapals Unit, available from Brookhaven Instruments Corp., Holtsville, N.Y. The Zeta potential of the SNOWTEX C control suspension was measured to be −25 millivolts. The Zeta potential of both the SNOWTEX C/copper chloride suspension and the SNOWTEX C/silver nitrate suspension were measured to be −11 millivolts. The Zeta potential of the SNOWTEX C/zinc chloride suspension was measured to be −8 millivolts. The difference in Zeta Potential between the solutions was evidence that the metal ions had adsorbed onto the silica nanoparticle.

A furfuryl mercaptan solution was prepared for testing the odor removal properties of the modified silica nanoparticles. A stock solution of 0.001 percent by weight furfural mercaptan solution, available from Aldrich Chemical Co., Milwaukee, Wis., was made in distilled water. The solution had a strong odor. High performance liquid chromatography (HPLC) was used to measure concentration changes. A Zorbax Eclipse XDB-C18, 4.6 by 150 millimeter, 5 micron column was used along with 100 percent acetonitrile eluent. One microliter of the furfuryl mercaptan solution was injected into the HPLC column with a flow rate of 0.25 milliliters/minute. The generated HPLC chromatogram demonstrated a furfuryl mercaptan peak to have an area of 16918 milliabsorption units·seconds (maus).

One drop of the SNOWTEX C/copper ion suspension was then added to 10 milliliters of the furfuryl mercaptan solution. The furfuryl mercaptan odor rapidly disappeared and one microliter of this furfuryl mercaptan solution was injected into the HPLC column with a flow rate of 0.25 milliliters/minute. The generated HPLC chromatogram showed the furfuryl mercaptan peak to have an area of 188 milliabsorption units·seconds (maus). The concentration of the furfuryl mercaptan was greatly reduced, and the detectable odor as well, with the addition of the modified nanoparticles.

Modified Nanoparticle Affinity for Odor Adsorption
Example 4

The SNOWTEX C/copper ion suspension was tested on human urine to determine the effectiveness in odor reduction. HPLC, as described in Example 3, was used to measure the components of urine (obtained from the inventor). One drop of the SNOWTEX C/copper ion suspension from Example 3 was tested against 0.1 gram of Purite Micronet MN-150 latex particles, available from Purolite Company, Philadelphia, Pa., and 0.1 gram of activated charcoal, available from Aldrich Chemical Co., Milwaukee, Wis. Each of these were added to a separate 3 grams of urine. The urine odor of the sample with the SNOWTEX C/copper ion suspension was almost completely eliminated after 3-5 seconds, compared to about 10 minutes for the activated charcoal. The latex particles never did remove the odor. Table 9 summarizes the comparison of the HPLC peaks for the 4 samples. The modified silica nanoparticles performed substantially better in removing the urine components than other materials.

TABLE 9

Urine component HPLC peaks (peak retention time (minutes))

| Sample | Area of peak at 3.87 min. | Area of peak at 4.04 min. | Area of peak at 4.77 min. | Area of peak at 5.64 min. | Area of peak at 5.88 min. | Area of peak at 6.23 min. |
| --- | --- | --- | --- | --- | --- | --- |
| Urine | 924 maus | 345 maus | 50 maus | 17 maus | 829 maus | 228 maus |
| Urine + Modified Silica Nanoparticles | 0 | 0 | 12 maus | 0 | 701 maus | 2 maus |
| Urine + Purite Latex Particles | 773 maus | 300 maus | 0 | 17 maus | 820 maus | 156 maus |
| Urine + Activated Charcoal | 900 maus | 0 | 50 maus | 17 maus | 820 maus | 10 maus |

Modified Nanoparticle Affinity for Odor Adsorption
Example 5

The odor removal properties of a modified nanoparticle when dry and coated on a surface was tested by coating a 10.16 centimeter square one-ply HI-COUNT® paper towel, available from Kimberly-Clark Corporation, Neenah, Wis., with the SNOWTEX C/copper ion suspension of Example 3 further diluted by 50 percent. The paper towel was coated by dipping the paper towel sample into the suspension. The wet paper towel was air-dried on a sheet of glass. The dried towel was placed over the mouth of a 100 milliliter beaker and held by a rubber band. The beaker contained 20 milliliter of the 0.001 percent by weight furfuryl mercaptan solution. A second untreated control HI-COUNT® paper towel was placed over an identical beaker as a control. The odors from the furfuryl mercaptans penetrated the untreated paper towel. However, no odors penetrated the paper towel treated with the modified nanoparticles for about three hours. After three hours the modified nanoparticles were saturated and the odors were detectable. The treated paper towel developed a dark area over the beaker during testing resulting from the binding of the furfuryl mercaptans.

Modified Nanoparticle Affinity for Odor Adsorption
Example 6

The odor removing properties of modified nanoparticles as an invisible coating on a bathroom tile was tested by treating a standard bathroom tile (15 centimeter×15 centimeter) from Home Depot with copper modified silica nanoparticles of Example 3. The suspension of copper modified silica nanoparticles was applied to a KIMWIPES® wiper. The moist KIMWIPES® wiper was used to wipe the bathroom tile surface and a second dry KIMWIPES® wiper was used to wipe off any excess liquid. 3.6 microliters of ammonia, 28 percent ammonia in water, available from Aldrich Chemical Co., Milwaukee, Wis., was introduced to a laboratory desiccator via syringe and after 10 minutes an aliquot of the air/odor was sampled and analyzed to determine the concentration of ammonia in the desiccator. The experiment was repeated three times; once with no tile in the desiccator, once with an untreated control tile in the desiccator, and once with the modified nanoparticle treated tile in the desiccator. The ammonia gas was measured by use of a Drager tube, available from SKC, Inc., Pennsylvania, which could measure ammonia in air concentrations from 2 to 30 parts per million. A volume of 60 milliliters of the air/odor was pulled out of the desiccator by means of a syringe. The Drager tube was connected by Tygon tubing between the desiccator and the syringe. The ammonia concentration in the desiccator was measured at 20 parts per million with no tile and with the untreated tile. The ammonia concentration in the desiccator with the modified nanoparticle treated tile was measured at less than 2 parts per million. The modified nanoparticles on the standard bathroom tile were effective in substantially reducing ammonia gas and odor.

Modified Nanoparticle Affinity for Odor Adsorption
Example 7

To demonstrate the odor removing properties of modified organic nanoparticles of this invention copper ions were adsorbed onto polystyrene nanoparticles. A dilute suspension of modified polystyrene nanoparticles was made by adding 1.0 milliliter of polystyrene nanoparticle suspension, the nanoparticles having a particle diameter of 64 nanometers, available from Polysciences, Inc., Warrington, Pa., to 9.0 milliliters of deionized water. The polystyrene nanoparticle suspension had a Zeta Potential of −49 millivolts, as measured by the Zetapals Unit as in Example 3. Two drops of 0.01 percent by weight copper chloride ($CuCl_2$) solution was added to the polystyrene nanoparticle suspension. After the addition of the 2 drops of copper chloride solution the Zeta Potential of the polystyrene solution was measured at −16 millivolts, thus confirming copper ion adsorption onto the polystyrene nanoparticles. One drop of the modified nanoparticle solution was added to a 2.0 milliliters of 0.001 percent by weight solution of furfuryl mercaptan. High performance liquid chromatography as described in Example 3 was used to measure furfuryl mercaptan presence before and after adding the modified nanoparticles. The area of the furfuryl mercaptan peak before the addition of the modified nanoparticles was 193 milliabsorption units and after the addition of the modified nanoparticles was 14 milliabsorption units. The copper modified polystyrene nanoparticles proved useful in removing sulphurous compounds.

Modified Nanoparticle Affinity for Odor Adsorption
Example 8

A dilute suspension of modified silica nanoparticles was made by adding 1 milliliter of SNOWTEX C, available from Nissan Chemical Industries, Ltd., Houston, Tex., to 9 milliliters of deionized water. The suspension was pipetted in equal portions into three different cuvets. Solutions of 0.01 percent by weight of each of copper chloride ($CuCl_2$), iron (II) chloride ($FeCl_2$), and iron (III) chloride ($FeCl_3$), all from Aldrich Chemical Company, Milwaukee, Wis., were prepared and one drop of each was added to a separate cuvet. The Zeta Potential of all three suspensions was then measured by a Zetapals Unit. The Zeta potential of the SNOWTEX C control suspension was measured to be −22 millivolts. The Zeta potential of the SNOWTEX C/copper chloride suspension was measured at −10 millivolts, the SNOWTEX C/iron (II) chloride suspension at −13 millivolts, and the SNOWTEX C/iron (III) chloride suspension at +13 millivolts. One drop of each of the modified nanoparticle solutions was added to a separate 2.0 milliliter solution of 0.001 percent by weight furfuryl mercaptan. High performance liquid chromatography as described in Example 3 was used to measure furfuryl mercaptan presence before and after adding the different modified nanoparticles. The results are summarized in Table 10. Each of the modified nanoparticles were successful in removing furfural mercaptan from the solution. Additionally, iron (III) ion modified silica nanoparticles had a positive Zeta Potential which can allow application to fabrics made from materials such as polypropylene, polyethylene, nylon, cotton, cellulosics, polyester, silk and wool, which have negative value streaming potentials.

TABLE 10

| Sample | Zeta Potential | Area of furfuryl mercaptan peak | Percent of odor removed |
|---|---|---|---|
| SNOWTEX C/$Cu^{+2}$ | −10 | 3.2 maus | 97% |
| SNOWTEX C/$Fe^{+2}$ | −13 | 38 maus | 67% |
| SNOWTEX C/$Fe^{+3}$ | +13 | 3.4 maus | 97% |

In the following Table 11, the adsorption of ammonia by various metal modified nanoparticles was comparatively evaluated. In particular, the analysis of dried modified nanoparticles confirmed that the nanoparticles are effective in removing triethylamine (TEA) odors. In conducting the review, a small amount of metal modified nanoparticle suspension was placed in a vial and allowed to air-dry at ambient conditions. A small dot of solid was left at the bottom of the vial. The Headspace test method as previously described was utilized in the analysis. Specifically, in conducting the analysis, the following procedure was followed.

1.0 ml of 0.01% by wt. of each of copper chloride ($CuCl_2$), iron (II) chloride (Fe (II) $Cl_2$), iron (III) chloride (Fe (III) $Cl_3$), silver nitrate ($AgNO_3$) and zinc chloride ($ZnCl_2$), all from Aldrich Chemical Company (Milwaukee, Wis.) were prepared and added to separate vials containing 1 ml of SNOWTEX-O (Nissan Chemical America, Houston Tex.). The vials were stirred 5 minutes. 10 mg of each of the solutions were then placed separately into GC headspace vials and the water allowed to evaporate over 2 days to leave a dry powder on the bottom of the vial. These vials were used to determine the amount of TEA absorbed using the GC headspace method. As controls, small amounts of activated carbon powder from MeadWestvaco (Covington, Va.) and Calgon were placed into separate GC headspace vials and also subjected to headspace testing. The unmodified silica (SNOWTEX-O) was also placed inot a GC headspace vial and allowed to air dry. The results in Table 11 show amine absorption.

TABLE 11

| Sample | Sample Weight (grams) | % Removed | Mg Odor Causing Chemical Removed/gram sample |
|---|---|---|---|
| Silica | 0.0055 | 13.0 | 50.7 |
| Copper/Silica | 0.0045 | 87.3 | 424.9 |
| Iron (II)/Silica | 0.0039 | 74.4 | 417.2 |
| Iron (III)/Silica | 0.0049 | 83.0 | 371.8 |
| Activated Carbon (Westvaco) | 0.0031 | 66.3 | 470.8 |
| Activated Carbon (Calgon) | 0.0034 | 36.8 | 234.7 |

It can be observed from the data that the TEA is efficiently removed by both the Copper and Iron III modified nanoparticles, while unmodified nanoparticles do a much less efficient job of TEA removal. For other chemistries, as illustrated in the following Tables 12, 13, and 14, other metals proved to be more efficient in removing the odors caused by other chemistries. For instance, ammonia adsorption experiments with metal modified silica nanoparticles demonstrated a high capacity of the modified nanoparticles for ammonia gas. Experiments with 1000 ppm ammonia did saturate the nanoparticles as can be seen in Table 12 below.

TABLE 12

| Sample | Ammonia Gas Detected (ppm) | % Removed |
|---|---|---|
| Control | 1000 | 0 |
| Iron (III) Silica | 220 | 78 |
| Copper/Silica | 210 | 80 |
| Silver/Silica | 160 | 84 |
| Zinc/Silica | 700 | 30 |
| KIMWIPES ® Control | 900 | 10 |

It can be observed from the data that zinc modified nanoparticles have little ability to remove ammonia gas, while silver modified nanoparticles have a very strong ability to remove ammonia gas.

The data in Table 13 below indicates a situation in which unmodified silica nanoparticles were optimal for removal of a specific chemical odor. For this study Silica, Silica/Copper and Silica/Iron (III) nanoparticle coated KIMWIPES® were analyzed for their ability to remove ketone and aldehyde odors. The results demonstrate that unmodified silica nanoparticles perform better for ketone odor removal than do copper or iron(III) modified silica nanoparticles. Specifically, the samples were tested for removal of 2,3-Butanedione.

TABLE 13

| Sample | % Removed | Mg Odor Causing Chemical Removed/gram sample |
|---|---|---|
| Silica (0.01 g) | 78.16 | 372 |
| Silica/Copper (0.01 g) | 18.85 | 99 |
| Silica/Iron (III) (0.01 g) | 17.33 | 82 |

Similarly, unmodified silica nanoparticles performed better for odor removal in removing aldehyde odors (3-methylbutanal) as can be seen in Table 14 below.

TABLE 14

| Sample | % Removed | Mg Odor Causing Chemical Removed/gram sample |
|---|---|---|
| Silica (0.01 g) | 21.52 | 90 |
| Silica/Copper (0.01 g) | 1.66 | 0 (approximately) |
| Silica/Iron (III) (0.01 g) | 0.99 | 0 (approximately) |

Modified Nanoparticle Affinity for Odor Adsorption
Example 9

This example illustrates the method of preparing a copper ion coating on a nanoparticle that has a high surface area (508 m2/g)

The potential to deposit copper hydroxide as an insoluble layer onto silica nanoparticles was successfully demonstrated. SNOWTEX-OXS (Nissan Chemical America, Houston, Tex.) a commercial 10% wt/wt suspension of 4-6 nm diameter nanoparticles was adjusted to pH 8.7 and a solution of copper chloride added with high shear mixing (10,000 rpm). The pH, Zeta potential and particle size were all monitored during addition of the copper salt. When a positive Zeta Potential was obtained the addition of copper salt was stopped. A control sample of copper hydroxide suspension was also prepared in a similar manner and the analytical results of the two studies shown in the Table 15 below.

TABLE 15

| SAMPLE | pH | Zeta Potential (mV) | Particle Size (nm) | Surface Area (m2/g) BET |
|---|---|---|---|---|
| SN-OXS | 8.7 | −55 | 9 | 509 |
| SN-OXS/Cu (II) | 8.6 | 38 | 43 | 508 |
| Cu(OH)2 | 8.5 | −8 | 36,735 | Not determined |

The above results demonstrate a coating of the copper hydroxide onto the SNOWTEX silica surface resulting in a positively charged particle having a good size (diameter). In contrast, the copper hydroxide formed in solution by itself formed large particles and remained negatively charged. The copper hydroxide coated silica sample retains the high surface area of the silica nanoparticle starting material.

In practicing blends of the current invention, it may be desirable, depending upon the specific product application, to apply the blends as part of a durable coating to a substrate (such as an packaging insert), which resists abrasion. The methodologies as described in the following examples, may be used to create such a coated insert.

Modified Nanoparticle as Part of Durable Coating
Example 10

Base sheet preparation: A dilute suspension of modified silica nanoparticles was made by adding SNOWTEX-AK nanoparticles from Nissan Chemical Industries to deionized water to produce a 2 weight percent solution. A solution of 5 weight percent copper chloride ($CuCl_2$) from Aldrich Chemical Company in an amount of 120 milliliters was added to 1120 ml of the 2 weight percent nanoparticle solution. Approximately 28.75 grams of Acid Blue 45, also from Aldrich Chemical Company was added to the above solution. A SCOTT® paper towel from Scott Paper Company of Mississauga, Ontario, Canada, was coated with the solution by dipping and allowed to dry in air at room temperature to produce an odor control sheet.

Durable coating: A solution containing 1 weight percent KYMENE 625 LX binder from Hercules Incorporated, Wilmington, Del., USA, was prepared. The base sheet was dipped in the KYMENE binder solution, passed through a nip to remove excess liquid and cured at 80° C. for one hour.

Durability Testing: Five repetitions of each sample of odor control base sheet and KYMENE binder treated sheet were tested according to the 30 second clean room standard testing protocol.

The 30 second clean room protocol is carried out in a room that meets class 100 clean room quality or better. A 23 cm by 23 cm sample is clamped between two holders that have a flexing stroke of 119.8 mm with a twist of 180 degrees at a rate of 60 cycles/minute. The stroke is affixed to the base of a Gelbo Flex unit, available from US Testing Co., Inc. of Hoboken, N.J., USA. The Flex unit is enclosed in a 1 cubic foot (28317 $cm^3$) box. An airflow of 1 cubic foot per minute flows through the box to a laser particle counter as the test proceeds. Laser particle counters include Model 200 L from Met One, Inc., of Grants Pass, Oreg., USA and Model C1-7350 from Climet Instrument Co. of Redlands, Calif., USA.

The results, in Table 16 below, show a decrease in the shedded particle counts after binder treatment, such as, for example, from 57,841 counts to 8557 counts for 0.5 micron size particles.

TABLE 16

| | Particle Count | |
|---|---|---|
| Particle Size | Base Sheet | Binder Treated Sheet |
| 10 microns | 100 | 108 |
| 5 microns | 417 | 174 |
| 1 micron | 18194 | 2465 |
| 0.7 microns | 35230 | 4813 |
| 0.5 microns | 57841 | 8557 |
| 0.3 microns | 78019 | 13362 |

Modified Nanoparticle as Part of Durable Coating
Example 11

A dilute suspension of modified silica nanoparticles was made by adding SNOWTEX-O nanoparticles from Nissan Chemical Industries to deionized water to produce a 2 weight percent solution. A second solution was prepared by adding 132.5 mg of polyethyleneimine (PEI) (Polysciences Inc.) having a molecular weight of about 1800, to 110 ml of deionized water. A 0.5 ml amount of the PEI solution was added to 300 ml of the nanoparticle solution with the further addition of $CuCl_2$ (Aldrich Chemical Company) in a sufficient amount to make a 0.067 weight percent solution of $CuCl_2$.

A SCOTT® HI-COUNT® paper towel was dipped in the resulting solution for 1 minute, passed through a nip to remove excess liquid and dried at room temperature. Durability Testing The treated SCOTT® HI-COUNT® towel, and a SCOTT® HI-COUNT® towel treated in a like manner but without PEI, were hung on a line and blown by an HT-800-19 series fan, manufactured by Honeywell of Southborough, Mass., USA at half speed for 24 hours. The fan-blown towels were analyzed by furnace elemental analysis to determine the silicon content before and after blowing. It was found by the analysis that the sample without PEI had lost about 9 percent of its Si content as a result of the fan blowing. The sample with PEI lost no silicon, indicating that the silica nanoparticles were well bonded to the towel. The odor removal capability was also tested and found to be essentially the same for each sample.

Product Application Example

In order to demonstrate the efficacy of including a blend of odor reducing nanoparticles within a product packaging, a small gauge hypodermic syringe was used to inject 1 ml of iron modified nanoparticle silica (20% active) into a cardboard roll core of a KLEENEX® COTTONELLE® Aloe and E 4 pack bathroom tissue package. After injection, tape was placed over the hole to seal the headspace. By utilizing SPME GC/MS on the headspace of the 4-pack, it was determined that the odor causing peak decreased by over 80 percent compared to a control in which distilled water was injected into the core. The same method of injection was used to add both unmodified and iron modified silica nanoparticles to KLEENEX® COTTONELLE® Aloe and E 4 pack bathroom tissue.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for neutralizing odor contained within the headspace of a product packaging comprising the steps of:
   a) formulating a blend comprising metal modified nanoparticles, wherein the metal modified nanoparticles are formed from silica, alumina, or a combination thereof;
   b) applying the blend to the inside of a product packaging.

2. The method of claim 1 further including the step of sealing the product packaging so as to maintain the environment inside the product packaging.

3. The method of claim 1 wherein the step of applying is comprised of applying the blend to an insert which is then placed within the product packaging.

4. The method of claim 1 wherein the step of applying is comprised of applying the blend to an inside surface of the product packaging.

5. The method of claim 1 wherein the step of applying is comprised of applying the blend to a portion of the product contained in the product packaging.

6. The method of claim 1 wherein the metal modified nanoparticles comprise at least two differently modified nanoparticles.

7. The method of claim 1 wherein the metal modified nanoparticles have an effective particle diameter of less than about 500 nanometers.

8. The method of claim 3 wherein the metal modified nanoparticles cover greater than about 50% of a surface of the insert.

9. The method of claim 1 wherein the nanoparticles are modified with a metal selected from the group consisting of copper, silver, gold, iron (II), iron (III), manganese, and combinations thereof.

10. The method of claim 1 wherein the metal modified nanoparticles are copper-modified silica nanoparticles.

11. The method of claim 1 wherein the metal modified nanoparticles have a surface area of at least about 200 square meters per gram.

12. The method of claim 1 wherein the metal modified nanoparticles have a surface area of at least about 500 square meters per gram.

13. The method of claim 1 wherein the blend further comprises unmodified nanoparticles.

14. A method for neutralizing odor contained within the headspace of product packaging for a rolled paper product containing a core, comprising the steps of:
   a) formulating a blend comprising metal modified nanoparticles;
   b) providing a rolled paper product containing a core;
   c) applying the blend to the inside surface of the core containing rolled paper product;
   d) enclosing the core containing rolled paper product within a product packaging.

15. The method of claim 14 wherein the metal modified nanoparticles comprise at least two differently modified nanoparticles.

16. The method of claim 14 wherein the blend further comprises unmodified nanoparticles.

17. A method for producing a packaged product which neutralizes head space odors contained within the product packaging comprises the steps of:
   a) providing a product to be packaged;
   b) packaging the product within a packaging material along with a blend comprising metal modified nanoparticles, wherein the metal modified nanoparticles are formed from silica, alumina, or a combination thereof; and
   c) enclosing the product within the packaging material.

18. The method of claim 17, wherein the blend is applied to an insert and the insert is enclosed with the product in the packaging.

19. The method of claim 17, wherein the packaging material has an inside surface and the blend is applied to the inside surface of the packaging material.

20. The method of claim 17, wherein the blend is enclosed with the product in the product packaging by being associated with the product.

21. The method of claim 17, wherein the blend further comprises unmodified nanoparticles.

22. The method of claim 17, wherein the metal modified nanoparticles comprise at least two differently modified nanoparticles.

* * * * *